US011740019B2

(12) United States Patent
Johnson et al.

(10) Patent No.: US 11,740,019 B2
(45) Date of Patent: Aug. 29, 2023

(54) LYOPHILIZATION LOADING TRAY ASSEMBLY AND SYSTEM

(71) Applicant: Terumo BCT Biotechnologies, LLC, Lakewood, CO (US)

(72) Inventors: Nathaniel T. Johnson, Highlands Ranch, CO (US); Dennis A. Bridges, Arvada, CO (US); Alexander Du Nguyen, Denver, CO (US); Margaret V. Kwiat, Evergreen, CO (US); Kestas P. Parakininkas, Englewood, CO (US); Rylan A. Summit, Denver, CO (US)

(73) Assignee: Terumo BCT Biotechnologies, LLC, Lakewood, CO (US)

( * ) Notice: Subject to any disclaimer, the term of this patent is extended or adjusted under 35 U.S.C. 154(b) by 0 days.

(21) Appl. No.: 18/073,217

(22) Filed: Dec. 1, 2022

(65) Prior Publication Data

US 2023/0098194 A1 Mar. 30, 2023

Related U.S. Application Data

(63) Continuation of application No. 16/815,880, filed on Mar. 11, 2020, now Pat. No. 11,604,026.
(Continued)

(51) Int. Cl.
*F26B 5/06* (2006.01)
*A61M 1/02* (2006.01)
(Continued)

(52) U.S. Cl.
CPC .............. *F26B 5/06* (2013.01); *A01N 1/0263* (2013.01); *A01N 1/0284* (2013.01);
(Continued)

(58) Field of Classification Search
CPC .. F26B 25/18; F26B 5/06; F26B 21/14; F26B 25/063; A61M 1/0277; A61M 2202/0415;
(Continued)

(56) References Cited

U.S. PATENT DOCUMENTS

| 136,036 A | 2/1873 | Craven |
| 1,441,570 A | 1/1923 | Fitzgerald |

(Continued)

FOREIGN PATENT DOCUMENTS

| AU | 517248 B2 | 7/1981 |
| AU | 590193 B2 | 11/1989 |

(Continued)

OTHER PUBLICATIONS

US 8,359,766 B2, 01/2013, Hubbard et al. (withdrawn)
(Continued)

*Primary Examiner* — Stephen M Gravini
(74) *Attorney, Agent, or Firm* — Harness, Dickey & Pierce, P.L.C.

(57) ABSTRACT

Provided is a loading tray assembly for housing a lyophilization container and a related system and method. The loading tray assembly includes a chassis including a contact void configured to facilitate direct contact between the attached lyophilization container and a lyophilizer shelf. The method includes securing a multi-part lyophilization container including a peelable seal on a lyophilization loading tray assembly, inputting a liquid into a non-breathable section of the lyophilization container, loading the tray assembly into a lyophilizer, freezing the liquid, applying heat energy and a vacuum, the vacuum causing an opening of the peelable seal and occluding the lyophilization container to isolate the frozen liquid.

20 Claims, 10 Drawing Sheets

Related U.S. Application Data

(60) Provisional application No. 62/971,072, filed on Feb. 6, 2020, provisional application No. 62/952,752, filed on Dec. 23, 2019, provisional application No. 62/818,214, filed on Mar. 14, 2019.

(51) Int. Cl.
| | | |
|---|---|---|
| *A01N 1/02* | (2006.01) | |
| *A61J 1/10* | (2006.01) | |
| *F26B 21/14* | (2006.01) | |
| *A61J 1/14* | (2023.01) | |
| *B65D 51/24* | (2006.01) | |
| *F26B 25/06* | (2006.01) | |
| *F26B 25/18* | (2006.01) | |

(52) U.S. Cl.
CPC .............. *A01N 1/0289* (2013.01); *A61J 1/10* (2013.01); *A61M 1/0277* (2014.02); *F26B 21/14* (2013.01); *A01N 1/0252* (2013.01); *A61J 1/1468* (2015.05); *A61M 2202/0415* (2013.01); *A61M 2205/3389* (2013.01); *A61M 2205/584* (2013.01); *B65D 51/241* (2013.01); *F26B 25/063* (2013.01); *F26B 25/18* (2013.01)

(58) Field of Classification Search
CPC .... A61M 2205/3389; A61M 2205/384; A01N 1/0263; A01N 1/284; A01N 1/289; A01N 1/252; B65D 51/241
USPC .............................................. 312/209; 34/90
See application file for complete search history.

(56) References Cited

U.S. PATENT DOCUMENTS

| | | |
|---|---|---|
| 1,504,225 A | 8/1924 | Fitzgerald |
| 1,956,784 A | 5/1934 | Allen |
| 2,659,986 A | 11/1953 | Hink, Jr. |
| 2,704,075 A | 3/1955 | Cherkin |
| 2,767,117 A | 10/1956 | Crawley |
| 2,893,843 A | 7/1959 | Adams, Jr. |
| 2,912,359 A | 11/1959 | Anigstein et al. |
| 3,008,879 A | 11/1961 | Harvill |
| 3,024,167 A | 3/1962 | Damaskus |
| 3,057,781 A | 10/1962 | Mace et al. |
| 3,123,443 A | 3/1964 | Smeby |
| 3,187,750 A | 6/1965 | Tenczar |
| 3,223,593 A | 12/1965 | Aldrich et al. |
| 3,228,841 A | 1/1966 | Cohen et al. |
| 3,229,813 A | 1/1966 | Crowe, Jr. et al. |
| 3,236,732 A | 2/1966 | Arquilla |
| 3,247,957 A | 4/1966 | Kemble |
| 3,260,648 A | 7/1966 | Fox |
| 3,294,523 A | 12/1966 | Morningstar |
| 3,322,634 A | 5/1967 | Fulthorpe |
| 3,375,824 A | 4/1968 | Krakauer et al. |
| 3,395,210 A | 7/1968 | Lenahan et al. |
| 3,423,290 A | 1/1969 | Chappelle |
| 3,453,180 A | 7/1969 | Fraser, Jr. et al. |
| 3,466,249 A | 9/1969 | Anderson |
| 3,468,471 A | 9/1969 | Linder |
| 3,490,437 A | 1/1970 | Bakondy et al. |
| 3,519,572 A | 7/1970 | Kita |
| 3,533,934 A | 10/1970 | Armanini |
| 3,537,189 A | 11/1970 | Bender et al. |
| 3,548,051 A | 12/1970 | DIngwall |
| 3,556,760 A | 1/1971 | Bender et al. |
| 3,565,987 A | 2/1971 | Schuurs |
| 3,571,940 A | 3/1971 | Bender |
| 3,573,063 A | 3/1971 | Williams |
| 3,574,950 A | 4/1971 | Dantoni |
| 3,607,858 A | 9/1971 | Querry et al. |
| 3,627,878 A | 12/1971 | Linsner |
| 3,629,142 A | 12/1971 | Marbach |
| 3,674,860 A | 7/1972 | Welter et al. |
| 3,714,345 A | 1/1973 | Hirata |
| 3,717,708 A | 2/1973 | Wada et al. |
| 3,730,843 A | 5/1973 | McKie, Jr. |
| 3,799,740 A | 3/1974 | Mincey |
| 3,803,299 A | 4/1974 | Nouel |
| 3,859,047 A | 1/1975 | Klein |
| 3,922,145 A | 11/1975 | Turner et al. |
| 3,932,943 A | 1/1976 | Briggs et al. |
| 3,944,665 A | 3/1976 | Galoian et al. |
| 3,945,523 A | 3/1976 | Wertlake et al. |
| 3,964,865 A | 6/1976 | Das |
| 3,973,002 A | 8/1976 | Hagan et al. |
| 3,987,159 A | 10/1976 | Spona et al. |
| 3,993,585 A | 11/1976 | Pinto et al. |
| 4,001,944 A | 1/1977 | Williams |
| 4,002,739 A | 1/1977 | Turner et al. |
| 4,035,924 A | 7/1977 | Faure |
| 4,045,176 A | 8/1977 | Proksch et al. |
| 4,049,673 A | 9/1977 | Scheinberg |
| 4,056,484 A | 11/1977 | Heimburger et al. |
| 4,059,491 A | 11/1977 | Iwasa et al. |
| 4,080,265 A | 3/1978 | Antonik |
| 4,089,944 A | 5/1978 | Thomas |
| 4,109,396 A | 8/1978 | Fraser |
| 4,127,502 A | 11/1978 | Li Mutti et al. |
| 4,134,943 A | 1/1979 | Knitsch et al. |
| 4,141,856 A | 2/1979 | Dorwart, Jr. et al. |
| 4,141,887 A | 2/1979 | Seufert |
| 4,155,186 A | 5/1979 | Robinson |
| 4,157,383 A | 6/1979 | Sedlacek et al. |
| 4,188,318 A | 2/1980 | Shanbrom |
| 4,189,400 A | 2/1980 | Proksch et al. |
| 4,202,665 A | 5/1980 | Wenz et al. |
| 4,218,321 A | 8/1980 | Sasaki et al. |
| 4,284,725 A | 8/1981 | Fennel, III et al. |
| 4,287,087 A | 9/1981 | Brinkhous et al. |
| 4,298,441 A | 11/1981 | Seidel et al. |
| 4,323,478 A | 4/1982 | Adams et al. |
| 4,324,685 A | 4/1982 | Louderback |
| 4,330,463 A | 5/1982 | Luijerink |
| 4,333,767 A | 6/1982 | Nass |
| 4,337,240 A | 6/1982 | Saklad |
| 4,442,655 A | 4/1984 | Stroetmann |
| 4,456,590 A | 6/1984 | Rubinstein |
| 4,465,774 A | 8/1984 | Huang et al. |
| 4,495,278 A | 1/1985 | Thomas |
| 4,543,335 A | 9/1985 | Sommer et al. |
| 4,581,231 A | 4/1986 | Purcell et al. |
| 4,595,021 A | 6/1986 | Shimizu et al. |
| 4,614,795 A | 9/1986 | Chavin et al. |
| 4,624,927 A | 11/1986 | Fukushima et al. |
| 4,650,678 A | 3/1987 | Fuhge et al. |
| 4,664,913 A | 5/1987 | Mielke et al. |
| 4,666,725 A | 5/1987 | Yamashita et al. |
| 4,687,664 A | 8/1987 | Philapitsch et al. |
| 4,716,119 A | 12/1987 | Rehner et al. |
| 4,722,790 A | 2/1988 | Cawley et al. |
| 4,730,460 A | 3/1988 | Coelho et al. |
| 4,731,330 A | 3/1988 | Hill et al. |
| 4,746,730 A | 5/1988 | De Ambrosi et al. |
| 4,780,314 A | 10/1988 | Graves |
| 4,802,286 A | 2/1989 | Kobayashi et al. |
| 4,806,343 A | 2/1989 | Carpenter et al. |
| 4,812,557 A | 3/1989 | Yasushi et al. |
| 4,813,210 A | 3/1989 | Masuda et al. |
| 4,850,353 A | 7/1989 | Stasz et al. |
| 4,874,690 A | 10/1989 | Goodrich, Jr. et al. |
| 4,877,608 A | 10/1989 | Lee et al. |
| 4,877,741 A | 10/1989 | Babcock et al. |
| 4,902,287 A | 2/1990 | Carmen et al. |
| 4,904,641 A | 2/1990 | Eibl et al. |
| 4,973,327 A | 11/1990 | Goodrich, Jr. et al. |
| 4,986,998 A | 1/1991 | Yoo et al. |
| 4,994,057 A | 2/1991 | Carmen et al. |
| 5,043,261 A | 8/1991 | Goodrich et al. |
| 5,045,446 A | 9/1991 | Goodrich, Jr. et al. |
| 5,059,036 A | 10/1991 | Richison et al. |
| 5,059,518 A | 10/1991 | Kortright et al. |

(56) References Cited

U.S. PATENT DOCUMENTS

| | | |
|---|---|---|
| 5,061,789 A | 10/1991 | Moller et al. |
| 5,063,178 A | 11/1991 | Toomey |
| 5,073,378 A | 12/1991 | Shoshan et al. |
| 5,114,004 A | 5/1992 | Isono et al. |
| 5,118,795 A | 6/1992 | Rubinstein |
| 5,147,803 A | 9/1992 | Enomoto |
| 5,151,500 A | 9/1992 | Wismer-Pedersen et al. |
| 5,171,661 A | 12/1992 | Goodrich, Jr. et al. |
| 5,178,884 A | 1/1993 | Goodrich et al. |
| 5,213,814 A | 5/1993 | Goodrich, Jr. et al. |
| 5,242,792 A | 9/1993 | Rudolph et al. |
| 5,257,983 A * | 11/1993 | Garyantes .......... F26B 5/06 604/408 |
| 5,260,420 A | 11/1993 | Burnouf-Radosevich et al. |
| 5,262,325 A | 11/1993 | Zimmermann et al. |
| 5,304,383 A | 4/1994 | Eibl et al. |
| 5,309,649 A | 5/1994 | Bergmann et al. |
| 5,340,592 A | 8/1994 | Goodrich, Jr. et al. |
| 5,399,670 A | 3/1995 | Bhattacharya et al. |
| 5,411,893 A | 5/1995 | Eden et al. |
| 5,420,250 A | 5/1995 | Lontz |
| 5,425,951 A | 6/1995 | Goodrich, Jr. et al. |
| 5,464,471 A | 11/1995 | Whalen et al. |
| 5,514,123 A | 5/1996 | Adolf et al. |
| 5,514,586 A | 5/1996 | Hottinger et al. |
| 5,527,260 A | 6/1996 | Kameyama |
| 5,547,873 A | 8/1996 | Magneson et al. |
| 5,551,781 A | 9/1996 | Wilkes et al. |
| 5,585,007 A | 12/1996 | Antanavich et al. |
| 5,637,345 A | 6/1997 | Lee et al. |
| 5,648,206 A | 7/1997 | Goodrich, Jr. et al. |
| 5,651,966 A | 7/1997 | Read et al. |
| 5,656,498 A | 8/1997 | Iijima et al. |
| 5,690,963 A | 11/1997 | Spargo et al. |
| 5,695,764 A | 12/1997 | Bontemps |
| 5,698,535 A | 12/1997 | Geczy et al. |
| 5,736,313 A | 4/1998 | Spargo et al. |
| 5,747,268 A | 5/1998 | Herring et al. |
| 5,750,330 A | 5/1998 | Tometsko et al. |
| 5,750,657 A | 5/1998 | Edwardson et al. |
| 5,759,774 A | 6/1998 | Hackett et al. |
| 5,795,571 A | 8/1998 | Cederholm-Williams et al. |
| 5,831,027 A | 11/1998 | McIntosh et al. |
| 5,834,418 A | 11/1998 | Brazeau et al. |
| 5,837,519 A | 11/1998 | Savage et al. |
| 5,849,473 A | 12/1998 | Cabrera et al. |
| 5,853,388 A | 12/1998 | Semel |
| 5,861,311 A | 1/1999 | Maples et al. |
| 5,891,393 A | 4/1999 | Read et al. |
| 5,919,766 A | 7/1999 | Osterberg et al. |
| 5,919,935 A | 7/1999 | Platz et al. |
| 5,946,931 A | 9/1999 | Lomax et al. |
| 5,964,043 A | 10/1999 | Oughton et al. |
| 5,968,831 A | 10/1999 | Shukla et al. |
| 5,985,582 A | 11/1999 | Triscott |
| 6,007,529 A | 12/1999 | Gustafsson et al. |
| 6,034,060 A | 3/2000 | Yamamoto et al. |
| 6,060,233 A | 5/2000 | Wiggins |
| 6,132,454 A | 10/2000 | Fellows |
| 6,139,878 A | 10/2000 | Summaria et al. |
| 6,148,536 A | 11/2000 | Iijima |
| 6,187,553 B1 | 2/2001 | Antignani et al. |
| 6,199,297 B1 * | 3/2001 | Wisniewski .......... F26B 5/06 206/439 |
| 6,218,195 B1 | 4/2001 | Gottschalk et al. |
| 6,221,575 B1 | 4/2001 | Roser et al. |
| 6,270,985 B1 | 8/2001 | Gottschalk et al. |
| 6,323,036 B1 | 11/2001 | Chapoteau et al. |
| 6,323,037 B1 | 11/2001 | Lauto et al. |
| 6,331,557 B1 | 12/2001 | Brugnara et al. |
| 6,346,216 B1 | 2/2002 | Kent |
| 6,350,584 B1 | 2/2002 | Gottschalk et al. |
| 6,358,236 B1 | 3/2002 | DeFoggi et al. |
| 6,358,678 B1 | 3/2002 | Bakaltcheva et al. |
| 6,372,423 B1 | 4/2002 | Braun |
| 6,381,870 B1 | 5/2002 | Kohlman et al. |
| 6,398,771 B1 | 6/2002 | Gustafsson et al. |
| 6,416,717 B1 | 7/2002 | Suzuki et al. |
| 6,472,162 B1 | 10/2002 | Coelho et al. |
| 6,517,526 B1 | 2/2003 | Tamari |
| 6,566,504 B2 | 5/2003 | Bhattacharya et al. |
| 6,608,237 B1 | 8/2003 | Li et al. |
| RE38,431 E | 2/2004 | Miekka et al. |
| 6,773,425 B1 | 8/2004 | Tamari |
| 6,852,540 B2 | 2/2005 | Makiuchi et al. |
| 6,869,901 B2 | 3/2005 | Lubker, II |
| 6,872,576 B1 | 3/2005 | McIntyre |
| 6,887,852 B1 | 5/2005 | Paik et al. |
| 6,890,512 B2 | 5/2005 | Roser et al. |
| 6,981,337 B2 | 1/2006 | Jones et al. |
| 7,041,635 B2 | 5/2006 | Kim et al. |
| 7,048,709 B2 | 5/2006 | Goudaliez et al. |
| 7,112,320 B1 | 9/2006 | Beaulieu et al. |
| 7,175,614 B2 | 2/2007 | Gollier et al. |
| 7,179,951 B2 | 2/2007 | Krishnaswamy-Mirle et al. |
| 7,202,341 B2 | 4/2007 | McGinnis et al. |
| 7,249,880 B2 | 7/2007 | Zambaux |
| 7,358,039 B2 | 4/2008 | Fischer et al. |
| 7,411,038 B2 | 8/2008 | Haynie |
| 7,422,726 B2 | 9/2008 | Hammerstedt et al. |
| 7,435,795 B2 | 10/2008 | McGinnis et al. |
| 7,473,246 B2 | 1/2009 | Vancaillie et al. |
| 7,480,032 B2 | 1/2009 | Braig et al. |
| 7,482,020 B2 | 1/2009 | Hennessy et al. |
| 7,501,493 B2 | 3/2009 | Roser |
| 7,569,184 B2 | 8/2009 | Wandell et al. |
| 7,618,406 B2 | 11/2009 | Roger |
| 7,678,888 B2 | 3/2010 | Friedman et al. |
| 7,727,743 B2 | 6/2010 | Bardat et al. |
| 7,776,022 B2 | 8/2010 | McCarthy et al. |
| 7,811,558 B2 | 10/2010 | Ho et al. |
| 7,879,332 B2 | 2/2011 | Zurlo et al. |
| 7,931,919 B2 | 4/2011 | Bakaltcheva et al. |
| 7,966,746 B2 * | 6/2011 | Py .......... F26B 5/06 514/1.9 |
| 8,057,872 B2 | 11/2011 | Chen |
| 8,097,403 B2 | 1/2012 | Ho et al. |
| 8,187,475 B2 | 5/2012 | Hecker et al. |
| 8,235,965 B2 | 8/2012 | Roger |
| 8,236,355 B2 | 8/2012 | Eijkenboom |
| 8,268,362 B2 | 9/2012 | Braun et al. |
| 8,277,837 B2 | 10/2012 | Fischer et al. |
| 8,313,654 B2 | 11/2012 | Piazza et al. |
| 8,372,343 B2 | 2/2013 | Goldstein |
| 8,377,882 B2 | 2/2013 | Schneider |
| 8,407,912 B2 | 4/2013 | Hubbard, Jr. et al. |
| 8,430,970 B2 | 4/2013 | Swami et al. |
| 8,449,520 B2 | 5/2013 | Pepper et al. |
| 8,450,079 B2 | 5/2013 | Kovalenko et al. |
| 8,491,178 B2 | 7/2013 | Breidenthal et al. |
| 8,492,081 B2 | 7/2013 | Nichols et al. |
| 8,512,754 B2 | 8/2013 | Needham |
| 8,516,714 B2 | 8/2013 | Biemans et al. |
| 8,518,452 B2 | 8/2013 | Bjornstrup et al. |
| 8,529,961 B2 | 9/2013 | Campbell et al. |
| 8,598,319 B2 | 12/2013 | Michel et al. |
| 8,603,063 B2 | 12/2013 | Grimm |
| 8,689,460 B2 | 4/2014 | Kuu |
| 8,858,681 B2 | 10/2014 | Harp |
| 8,951,565 B2 | 2/2015 | McCarthy |
| 9,011,846 B2 | 4/2015 | Overholser et al. |
| 9,046,303 B2 | 6/2015 | Yagi |
| 9,132,206 B2 | 9/2015 | McCarthy |
| 9,161,527 B2 | 10/2015 | Cutting et al. |
| 9,545,379 B2 | 1/2017 | Liu et al. |
| 9,561,184 B2 | 2/2017 | Khan et al. |
| 9,561,893 B2 | 2/2017 | Root et al. |
| 9,696,284 B2 | 7/2017 | Rannisto et al. |
| 10,451,346 B1 | 10/2019 | Nguyen |
| 10,507,165 B2 | 12/2019 | Di Naro |
| 10,539,367 B2 | 1/2020 | Corbin, III et al. |
| 10,793,327 B2 | 10/2020 | Weimer |
| 11,279,510 B2 | 3/2022 | Root et al. |
| 11,604,026 B2 * | 3/2023 | Johnson .......... A61M 1/0277 |

(56) References Cited

U.S. PATENT DOCUMENTS

| | | |
|---|---|---|
| 11,609,043 B2 * | 3/2023 | Johnson .................. F26B 5/06 |
| 2001/0004641 A1 | 6/2001 | Hawkins |
| 2001/0031721 A1 | 10/2001 | Webb et al. |
| 2002/0035354 A1 | 3/2002 | Mirle et al. |
| 2002/0146409 A1 | 10/2002 | Herring et al. |
| 2003/0065149 A1 | 4/2003 | McGinnis et al. |
| 2003/0068416 A1 | 4/2003 | Burgess et al. |
| 2003/0080056 A1 | 5/2003 | Boos et al. |
| 2003/0104508 A1 | 6/2003 | Gempeler et al. |
| 2003/0134418 A1 | 7/2003 | Mitaka |
| 2003/0143566 A1 | 7/2003 | Helftenbein |
| 2004/0005310 A1 | 1/2004 | Rapp et al. |
| 2004/0081588 A1 | 4/2004 | Hammerstedt et al. |
| 2004/0126880 A1 | 7/2004 | Manders et al. |
| 2004/0132207 A1 | 7/2004 | Arima et al. |
| 2005/0158856 A1 | 7/2005 | Edelson et al. |
| 2005/0170068 A1 | 8/2005 | Roodink et al. |
| 2005/0282734 A1 | 12/2005 | Kadima et al. |
| 2006/0004189 A1 | 1/2006 | Gandy |
| 2006/0134084 A1 | 6/2006 | Wolkers et al. |
| 2006/0182652 A1 | 8/2006 | Burgess et al. |
| 2006/0216687 A1 | 9/2006 | Alves-Filho et al. |
| 2006/0263759 A1 | 11/2006 | Alves-Filho et al. |
| 2007/0014780 A1 | 1/2007 | Woolverton |
| 2007/0022622 A1 | 2/2007 | Lanaway et al. |
| 2007/0110817 A1 | 5/2007 | Shestakov |
| 2007/0135343 A1 | 6/2007 | Webb et al. |
| 2007/0166389 A1 | 7/2007 | Bakaltcheva |
| 2007/0275028 A1 | 11/2007 | Barry et al. |
| 2008/0038818 A1 | 2/2008 | Natan et al. |
| 2008/0063697 A1 | 3/2008 | Bedard |
| 2008/0145444 A1 | 6/2008 | Merchant et al. |
| 2008/0193386 A1 | 8/2008 | Yoo et al. |
| 2008/0206293 A1 | 8/2008 | Toreki et al. |
| 2008/0234653 A1 | 9/2008 | McCarthy et al. |
| 2008/0234654 A1 | 9/2008 | McCarthy et al. |
| 2008/0249499 A1 | 10/2008 | Vancaillie et al. |
| 2008/0256822 A1 | 10/2008 | Suzuki et al. |
| 2008/0299212 A1 | 12/2008 | Kim et al. |
| 2009/0019724 A1 | 1/2009 | Wagner et al. |
| 2009/0036862 A1 | 2/2009 | Grimm |
| 2009/0107001 A1 | 4/2009 | McCarthy |
| 2009/0113753 A1 | 5/2009 | Pepper et al. |
| 2009/0223080 A1 | 9/2009 | McCarthy et al. |
| 2009/0324929 A1 | 12/2009 | Yamakawa et al. |
| 2010/0049156 A1 | 2/2010 | Dickhorner et al. |
| 2010/0144595 A1 | 6/2010 | Bucci |
| 2010/0159023 A1 | 6/2010 | Bjornstrup et al. |
| 2010/0168018 A1 | 7/2010 | Pikal et al. |
| 2011/0008458 A1 | 1/2011 | Gandy et al. |
| 2011/0008459 A1 | 1/2011 | Marguerre et al. |
| 2011/0020299 A1 | 1/2011 | Bader |
| 2011/0114524 A1 | 5/2011 | Eibl |
| 2011/0142948 A1 | 6/2011 | Langer et al. |
| 2011/0144613 A1 | 6/2011 | Pepper et al. |
| 2011/0177541 A1 | 7/2011 | Martinoli et al. |
| 2011/0183311 A1 | 7/2011 | Ho et al. |
| 2011/0263408 A1 | 10/2011 | Suto et al. |
| 2011/0282325 A1 | 11/2011 | Gregory |
| 2012/0027867 A1 | 2/2012 | Fischer et al. |
| 2012/0040384 A1 | 2/2012 | Stangier |
| 2012/0045518 A1 | 2/2012 | Nielsen et al. |
| 2012/0070855 A1 | 3/2012 | Mirshahi et al. |
| 2012/0141595 A1 | 6/2012 | Tseng et al. |
| 2012/0156306 A1 | 6/2012 | Weissman et al. |
| 2012/0231485 A1 | 9/2012 | Onundarson et al. |
| 2012/0252044 A1 | 10/2012 | Rechner et al. |
| 2012/0329082 A1 | 12/2012 | Viola et al. |
| 2013/0008048 A1 | 1/2013 | Patel et al. |
| 2013/0019572 A1 | 1/2013 | Beator et al. |
| 2013/0030161 A1 | 1/2013 | Anitua Aldecoa |
| 2013/0040890 A1 | 2/2013 | Guo et al. |
| 2013/0090291 A1 | 4/2013 | Gulle et al. |
| 2013/0116410 A1 | 5/2013 | Ivarsson et al. |
| 2013/0122107 A1 | 5/2013 | Bakaltcheva |
| 2013/0143198 A1 | 6/2013 | Sailliol |
| 2013/0149727 A1 | 6/2013 | Aygen |
| 2013/0183661 A1 | 7/2013 | Prante et al. |
| 2013/0195897 A1 | 8/2013 | Teschner et al. |
| 2013/0195959 A1 | 8/2013 | Patel |
| 2013/0202585 A1 | 8/2013 | Bardat et al. |
| 2013/0243877 A1 | 9/2013 | Haley et al. |
| 2013/0251695 A1 | 9/2013 | Farmer et al. |
| 2013/0303842 A1 | 11/2013 | Zeitels et al. |
| 2013/0316011 A1 | 11/2013 | Ahn et al. |
| 2013/0326899 A1 | 12/2013 | Yagi |
| 2014/0212895 A1 | 7/2014 | Lim |
| 2014/0259724 A1 | 9/2014 | McCarthy et al. |
| 2014/0287643 A1 | 9/2014 | Nozaki et al. |
| 2014/0360891 A1 | 12/2014 | Kline et al. |
| 2016/0084572 A1 | 3/2016 | Khan et al. |
| 2016/0375184 A1 | 12/2016 | Albert et al. |
| 2017/0100339 A1 | 4/2017 | Liu et al. |
| 2017/0113824 A1 | 4/2017 | Root et al. |
| 2017/0203871 A1 | 7/2017 | Murto et al. |
| 2017/0258877 A1 | 9/2017 | Bare et al. |
| 2017/0259186 A1 | 9/2017 | Khan et al. |
| 2017/0367322 A1 | 12/2017 | Liu et al. |
| 2018/0128544 A1 | 5/2018 | Corbin, III et al. |
| 2019/0000979 A1 | 1/2019 | Cleek et al. |
| 2019/0030169 A1 | 1/2019 | Ivarsson et al. |
| 2019/0142694 A1 | 5/2019 | Di Naro |
| 2020/0289728 A1 | 9/2020 | Johnson |
| 2022/0087900 A1 | 3/2022 | Taha et al. |
| 2023/0098194 A1 * | 3/2023 | Johnson .............. A61M 1/0277 |
| | | 312/209 |

FOREIGN PATENT DOCUMENTS

| | | |
|---|---|---|
| AU | 622133 B2 | 4/1992 |
| AU | 8165698 A | 1/2000 |
| AU | 744025 B2 | 2/2002 |
| AU | 2002326819 A1 | 4/2003 |
| AU | 2007205748 B2 | 11/2009 |
| AU | 2012205238 A1 | 8/2012 |
| BG | 64922 B1 | 9/2006 |
| CA | 745958 A | 11/1966 |
| CA | 780792 A | 3/1968 |
| CA | 787838 A | 6/1968 |
| CA | 835939 A | 3/1970 |
| CA | 843883 A | 6/1970 |
| CA | 1260389 A | 9/1989 |
| CN | 1210267 A | 3/1999 |
| CN | 1242429 A | 1/2000 |
| CN | 1376520 A | 10/2002 |
| CN | 1410537 A | 4/2003 |
| CN | 1156282 C | 7/2004 |
| CN | 1157194 C | 7/2004 |
| CN | 1162160 C | 8/2004 |
| CN | 1187616 C | 2/2005 |
| CN | 1220512 C | 9/2005 |
| CN | 1745627 A | 3/2006 |
| CN | 1250718 C | 4/2006 |
| CN | 1267340 C | 8/2006 |
| CN | 1270731 C | 8/2006 |
| CN | 1281161 C | 10/2006 |
| CN | 1931025 A | 3/2007 |
| CN | 101152211 A | 4/2008 |
| CN | 101216432 A | 7/2008 |
| CN | 101299029 A | 11/2008 |
| CN | 101310728 A | 11/2008 |
| CN | 100469359 C | 3/2009 |
| CN | 101416985 A | 4/2009 |
| CN | 100531723 C | 8/2009 |
| CN | 101579356 A | 11/2009 |
| CN | 100584942 C | 1/2010 |
| CN | 101618120 A | 1/2010 |
| CN | 101167745 B | 6/2010 |
| CN | 101766252 A | 7/2010 |
| CN | 101833009 A | 9/2010 |
| CN | 101879333 A | 11/2010 |
| CN | 101893628 A | 11/2010 |
| CN | 101893639 A | 11/2010 |
| CN | 101957364 A | 1/2011 |

(56) References Cited

FOREIGN PATENT DOCUMENTS

| | | |
|---|---|---|
| CN | 101971972 A | 2/2011 |
| CN | 101347617 B | 4/2011 |
| CN | 102000022 A | 4/2011 |
| CN | 102008504 A | 4/2011 |
| CN | 102012433 A | 4/2011 |
| CN | 102050876 A | 5/2011 |
| CN | 102078306 A | 6/2011 |
| CN | 102106872 A | 6/2011 |
| CN | 101433553 B | 8/2011 |
| CN | 102207504 A | 10/2011 |
| CN | 101385855 B | 11/2011 |
| CN | 102229670 A | 11/2011 |
| CN | 102241767 A | 11/2011 |
| CN | 102250238 A | 11/2011 |
| CN | 101461939 B | 1/2012 |
| CN | 102337252 A | 2/2012 |
| CN | 102363634 A | 2/2012 |
| CN | 102426240 A | 4/2012 |
| CN | 102426258 A | 4/2012 |
| CN | 101285086 B | 5/2012 |
| CN | 102435743 A | 5/2012 |
| CN | 101830979 B | 6/2012 |
| CN | 101843335 B | 6/2012 |
| CN | 102507934 A | 6/2012 |
| CN | 102512418 A | 6/2012 |
| CN | 102524812 A | 7/2012 |
| CN | 102552154 A | 7/2012 |
| CN | 102579737 A | 7/2012 |
| CN | 102590496 A | 7/2012 |
| CN | 102590529 A | 7/2012 |
| CN | 102600074 A | 7/2012 |
| CN | 102600231 A | 7/2012 |
| CN | 102600508 A | 7/2012 |
| CN | 101899110 B | 8/2012 |
| CN | 102614219 A | 8/2012 |
| CN | 102628869 A | 8/2012 |
| CN | 102645358 A | 8/2012 |
| CN | 101816789 B | 9/2012 |
| CN | 102688200 A | 9/2012 |
| CN | 102692514 A | 9/2012 |
| CN | 101900712 B | 10/2012 |
| CN | 102327289 B | 10/2012 |
| CN | 102697581 A | 10/2012 |
| CN | 102746396 A | 10/2012 |
| CN | 102754848 A | 10/2012 |
| CN | 102327288 B | 11/2012 |
| CN | 102793053 A | 11/2012 |
| CN | 101843289 B | 12/2012 |
| CN | 102854322 A | 1/2013 |
| CN | 102866220 A | 1/2013 |
| CN | 102866255 A | 1/2013 |
| CN | 102879560 A | 1/2013 |
| CN | 101948630 B | 2/2013 |
| CN | 102908321 A | 2/2013 |
| CN | 102908368 A | 2/2013 |
| CN | 102093385 B | 3/2013 |
| CN | 102228683 B | 3/2013 |
| CN | 102240310 B | 3/2013 |
| CN | 102988974 A | 3/2013 |
| CN | 102210854 B | 4/2013 |
| CN | 103007280 A | 4/2013 |
| CN | 103039693 A | 4/2013 |
| CN | 103054816 A | 4/2013 |
| CN | 101756013 B | 5/2013 |
| CN | 103076455 A | 5/2013 |
| CN | 103113456 A | 5/2013 |
| CN | 102258780 B | 6/2013 |
| CN | 102319425 B | 6/2013 |
| CN | 102525954 B | 6/2013 |
| CN | 102274493 B | 8/2013 |
| CS | 277138 B6 | 11/1992 |
| DE | 109659 A1 | 11/1974 |
| DE | 2430447 A1 | 1/1975 |
| DE | 112775 A1 | 5/1975 |
| DE | 2617742 A1 | 6/1977 |
| DE | 2365629 C2 | 6/1983 |
| DE | 19729778 A1 | 1/1999 |
| DE | 69521470 T2 | 5/2002 |
| DE | 69133198 T2 | 7/2003 |
| DE | 69810755 T2 | 8/2003 |
| EP | 105923 A1 | 4/1984 |
| EP | 121868 A1 | 10/1984 |
| EP | 111777 B1 | 3/1987 |
| EP | 0124018 B1 | 11/1987 |
| EP | 204045 A3 | 1/1988 |
| EP | 0284249 A1 | 9/1988 |
| EP | 0335682 A1 | 10/1989 |
| EP | 0343596 A2 | 11/1989 |
| EP | 206448 B1 | 11/1990 |
| EP | 215050 B1 | 2/1991 |
| EP | 445108 A1 | 9/1991 |
| EP | 392377 B1 | 2/1995 |
| EP | 593176 A3 | 3/1995 |
| EP | 752097 A1 | 1/1997 |
| EP | 485377 B1 | 5/1999 |
| EP | 1021726 A1 | 7/2000 |
| EP | 1087990 A1 | 4/2001 |
| EP | 1171163 A1 | 1/2002 |
| EP | 1243275 A1 | 9/2002 |
| EP | 1286706 A2 | 3/2003 |
| EP | 876155 B1 | 7/2004 |
| EP | 1113269 B1 | 10/2006 |
| EP | 1870649 A1 | 12/2007 |
| EP | 997735 B1 | 1/2008 |
| EP | 1958618 A1 | 8/2008 |
| EP | 1730299 B1 | 6/2011 |
| EP | 2371343 A3 | 12/2011 |
| EP | 2574350 A1 | 4/2013 |
| EP | 1407780 A1 | 5/2013 |
| FR | 2001727 A1 | 10/1969 |
| FR | 2160285 A1 | 6/1973 |
| FR | 2187909 A1 | 1/1974 |
| FR | 2224118 A1 | 10/1974 |
| FR | 2227276 A1 | 11/1974 |
| FR | 2363577 A1 | 3/1978 |
| FR | 2475737 A1 | 8/1981 |
| FR | 2600998 A1 | 1/1988 |
| FR | 2729932 A1 | 8/1996 |
| FR | 2814239 A1 | 3/2002 |
| FR | 2963556 A3 | 2/2012 |
| GB | 353286 A | 7/1931 |
| GB | 425567 A | 3/1935 |
| GB | 450146 A | 7/1936 |
| GB | 491515 A | 9/1938 |
| GB | 620573 A | 3/1949 |
| GB | 727148 A | 3/1955 |
| GB | 731104 A | 6/1955 |
| GB | 748784 A | 5/1956 |
| GB | 770075 A | 3/1957 |
| GB | 807781 A | 1/1959 |
| GB | 814491 A | 6/1959 |
| GB | 853288 A | 11/1960 |
| GB | 859609 A | 1/1961 |
| GB | 906860 A | 9/1962 |
| GB | 911181 A | 11/1962 |
| GB | 917012 A | 1/1963 |
| GB | 941019 A | 11/1963 |
| GB | 979759 A | 1/1965 |
| GB | 1003748 A | 9/1965 |
| GB | 1073172 A | 6/1967 |
| GB | 1074461 A | 7/1967 |
| GB | 1186544 A | 4/1970 |
| GB | 1206033 A | 9/1970 |
| GB | 1222810 A | 2/1971 |
| GB | 1266274 A | 3/1972 |
| GB | 1337178 A | 11/1973 |
| GB | 1372812 A | 11/1974 |
| GB | 1391746 A | 4/1975 |
| GB | 1480092 A | 7/1977 |
| GB | 1486787 A | 9/1977 |
| GB | 1497517 A | 1/1978 |
| GB | 1507435 A | 4/1978 |
| GB | 1524712 A | 9/1978 |
| GB | 1530748 A | 11/1978 |

(56) References Cited

FOREIGN PATENT DOCUMENTS

| | | |
|---|---|---|
| GB | 1536725 A | 12/1978 |
| GB | 1551792 A | 8/1979 |
| GB | 1551928 A | 9/1979 |
| GB | 1563839 A | 4/1980 |
| GB | 2148090 B | 7/1987 |
| GB | 2167856 B | 12/1988 |
| IT | 1064142 B | 2/1985 |
| JP | S52156921 A | 12/1977 |
| JP | S53091117 A | 8/1978 |
| JP | S5426961 A | 2/1979 |
| JP | S5571452 A | 5/1980 |
| JP | S56127307 A | 10/1981 |
| JP | S56127308 A | 10/1981 |
| JP | S56160991 A | 12/1981 |
| JP | S5772911 A | 5/1982 |
| JP | S57122796 A | 7/1982 |
| JP | S57142561 A | 9/1982 |
| JP | S57159561 A | 10/1982 |
| JP | S58131566 A | 8/1983 |
| JP | S59088042 A | 5/1984 |
| JP | S59136657 A | 8/1984 |
| JP | S59181224 A | 10/1984 |
| JP | S59212768 A | 12/1984 |
| JP | S59218960 A | 12/1984 |
| JP | S60168051 A | 8/1985 |
| JP | S61040752 A | 2/1986 |
| JP | S61053567 A | 3/1986 |
| JP | S61128974 A | 6/1986 |
| JP | S61155332 A | 7/1986 |
| JP | S61225652 A | 10/1986 |
| JP | S61282054 A | 12/1986 |
| JP | S62010019 A | 1/1987 |
| JP | S62138433 A | 6/1987 |
| JP | H63-036828 A | 2/1988 |
| JP | S63157936 A | 6/1988 |
| JP | 1021741 B | 4/1989 |
| JP | H1247060 A | 10/1989 |
| JP | H2221859 A | 9/1990 |
| JP | H07270405 A | 10/1995 |
| JP | H09020687 A | 1/1997 |
| JP | H09222427 A | 8/1997 |
| JP | 2657092 B2 | 9/1997 |
| JP | H1045616 A | 2/1998 |
| JP | H10108907 A | 4/1998 |
| JP | 3140797 B2 | 3/2001 |
| JP | 3142192 B2 | 3/2001 |
| JP | 3219181 B2 | 10/2001 |
| JP | 2002029977 A | 1/2002 |
| JP | 2002052067 A | 2/2002 |
| JP | 3292760 B2 | 6/2002 |
| JP | 3365091 B2 | 1/2003 |
| JP | 2003055256 A | 2/2003 |
| JP | 2003055257 A | 2/2003 |
| JP | 2003339346 A | 12/2003 |
| JP | 2004049493 A | 2/2004 |
| JP | 3543144 B2 | 7/2004 |
| JP | 3712989 B2 | 11/2005 |
| JP | 2006036749 A | 2/2006 |
| JP | 2007197353 A | 8/2007 |
| JP | 4024506 B2 | 12/2007 |
| JP | 4059299 B2 | 3/2008 |
| JP | 2006545011-X | 5/2008 |
| JP | 2008527741 A | 7/2008 |
| JP | 2009297212 A | 12/2009 |
| JP | 2010266086 A | 11/2010 |
| JP | 2011239 A | 1/2011 |
| JP | 2011120763 A | 6/2011 |
| JP | 2012051895 A | 3/2012 |
| JP | 5002106 B2 | 8/2012 |
| JP | 5037621 B2 | 10/2012 |
| JP | 5049447 B2 | 10/2012 |
| JP | 5087815 B2 | 12/2012 |
| JP | 5252909 B2 | 7/2013 |
| JP | 5340945 B2 | 11/2013 |
| JP | 2014-028661 A | 2/2014 |
| JP | 5960660 B2 | 8/2016 |
| JP | 6219922 B2 | 10/2017 |
| JP | 6305870 B2 | 4/2018 |
| KR | 100197297 B1 | 6/1999 |
| KR | 20000020804 A | 4/2000 |
| KR | 100503629 B1 | 7/2005 |
| KR | 20060005770 A | 1/2006 |
| KR | 100631188 B1 | 10/2006 |
| KR | 100767541 B1 | 10/2007 |
| KR | 100857273 B1 | 9/2008 |
| KR | 100908742 B1 | 7/2009 |
| KR | 20110008382 A | 1/2011 |
| KR | 101157096 B1 | 6/2012 |
| KR | 101200423 B1 | 11/2012 |
| KR | 20130009161 A | 1/2013 |
| KR | 20130034991 A | 4/2013 |
| KR | 20130053609 A | 5/2013 |
| RU | 2011202 C1 | 4/1994 |
| RU | 2028130 C1 | 2/1995 |
| RU | 2028133 C1 | 2/1995 |
| RU | 2080865 C1 | 6/1997 |
| RU | 2090165 C1 | 9/1997 |
| RU | 2090166 C1 | 9/1997 |
| RU | 2121364 C1 | 11/1998 |
| RU | 2193868 C2 | 12/2002 |
| RU | 2197267 C1 | 1/2003 |
| RU | 2242759 C1 | 12/2004 |
| RU | 2266542 C1 | 12/2005 |
| RU | 2273026 C1 | 3/2006 |
| RU | 2314527 C1 | 1/2008 |
| RU | 2322243 C1 | 4/2008 |
| RU | 2332666 C1 | 8/2008 |
| RU | 2325655 C9 | 11/2008 |
| RU | 2357252 C1 | 5/2009 |
| RU | 2426548 C2 | 8/2011 |
| RU | 2442984 C1 | 2/2012 |
| RU | 2455014 C1 | 7/2012 |
| RU | 2456602 C1 | 7/2012 |
| RU | 2463063 C1 | 10/2012 |
| RU | 2012137892 A | 2/2013 |
| RU | 2478958 C1 | 4/2013 |
| RU | 2492867 C1 | 9/2013 |
| SU | 548275 A1 | 2/1977 |
| SU | 654238 A1 | 3/1979 |
| SU | 686732 A1 | 9/1979 |
| SU | 700129 A1 | 11/1979 |
| SU | 786954 A1 | 12/1980 |
| SU | 1344354 A1 | 10/1987 |
| SU | 1592717 A1 | 9/1990 |
| SU | 1678371 A1 | 9/1991 |
| SU | 1716443 A1 | 2/1992 |
| SU | 1752187 A3 | 7/1992 |
| TW | 200600103 A | 1/2006 |
| TW | I358264 B | 2/2012 |
| UA | 26543 U | 9/2007 |
| WO | WO-1992013495 A1 | 8/1992 |
| WO | WO-1992014360 A1 | 9/1992 |
| WO | WO-1995012127 A1 | 5/1995 |
| WO | WO-1995015763 A1 | 6/1995 |
| WO | WO-1995-027180 A1 | 10/1995 |
| WO | WO-1996/29556 A1 | 9/1996 |
| WO | WO-1996-031748 A1 | 10/1996 |
| WO | WO-1997046883 A1 | 12/1997 |
| WO | WO-2000-036353 A1 | 6/2000 |
| WO | WO-2000047187 A1 | 8/2000 |
| WO | WO-2001064228 A1 | 9/2001 |
| WO | WO-2002083157 A1 | 10/2002 |
| WO | WO-2002083737 A1 | 10/2002 |
| WO | WO-2002087540 A1 | 11/2002 |
| WO | WO-2003082310 A1 | 10/2003 |
| WO | WO-2006000422 A1 | 1/2006 |
| WO | WO-2006028648 A2 | 3/2006 |
| WO | WO-2006054519 A1 | 5/2006 |
| WO | WO-2007104760 A2 | 9/2007 |
| WO | WO-2008108549 A1 | 9/2008 |
| WO | WO-2008115548 A2 | 9/2008 |
| WO | WO-2008-130602 A1 | 10/2008 |

(56) References Cited

FOREIGN PATENT DOCUMENTS

| WO | WO-2010019217 A1 | 2/2010 |
| WO | WO-2010033169 A1 | 3/2010 |
| WO | WO-2010093429 A1 | 8/2010 |
| WO | WO-2012092712 A1 | 7/2012 |
| WO | WO-2012098358 A1 | 7/2012 |
| WO | WO-2012101109 A1 | 8/2012 |
| WO | WO-2012140209 A1 | 10/2012 |
| WO | WO-2012159075 A1 | 11/2012 |
| WO | WO-2013013537 A1 | 1/2013 |
| WO | WO-2013042868 A1 | 3/2013 |
| WO | WO-2013057219 A1 | 4/2013 |
| WO | WO-2013-062479 A1 | 5/2013 |
| WO | WO-2013076507 A2 | 5/2013 |
| WO | WO-2013085502 A1 | 6/2013 |
| WO | WO-2014033228 A1 | 3/2014 |
| WO | WO-2014-165222 A1 | 10/2014 |
| WO | WO-2015191599 A3 | 4/2016 |
| WO | WO-2020185909 A3 | 12/2020 |
| WO | WO-2020242552 A1 | 12/2020 |

OTHER PUBLICATIONS

Cannon, Jeremy W. M.D., "Prehospital Damage-Control Resuscitation", The New England Journal of Medicine, Jul. 26, 2018, pp. 387-388.

Cherry, Chris, "Containment systems for freeze-drying," ISL-FD, Sep. 7, 2015.

Cherry, Christopher Lee Albert, "Development of Novel Containment Systems for Freeze-Drying," a thesis submitted to Cardiff Metropolitan University, Apr. 10, 2013.

Glassberg et al, Freeze-dried Plasma al the Point of Injury: from Concept lo Doctrine, Shock, Dec. 2013, vol. 40, No. 6, pp. 444-450.

Pan et al, "Study of Banana Dehydration Using Sequential Infrared Radiation Heating and Freeze-Drying", LWT—Food Science and Technology, 2008 v. 41, pp. 1944-1951.

Soares, Jeffrey M., "Saving Lives with Freeze-dried Plasma", The United States Army, Nov. 27, 2017, pp. 1-5. 1tlps://www.army.mil/article/197409.

Sperry et al, "Prehospital Plasma during Air Medical Transport in Trauma Patients at Risk for Hemorrhagic Shock", The New England Journal of Medicine. Jul. 26, 2018, pp. 315-326.

\* cited by examiner

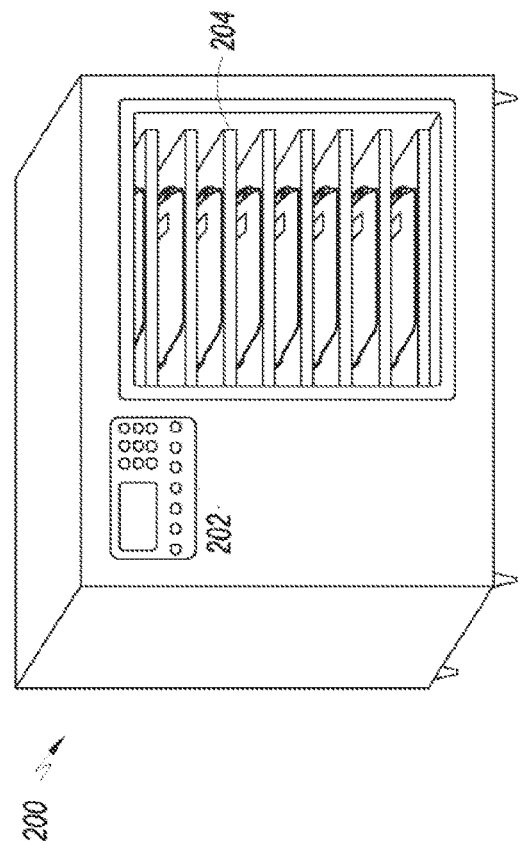
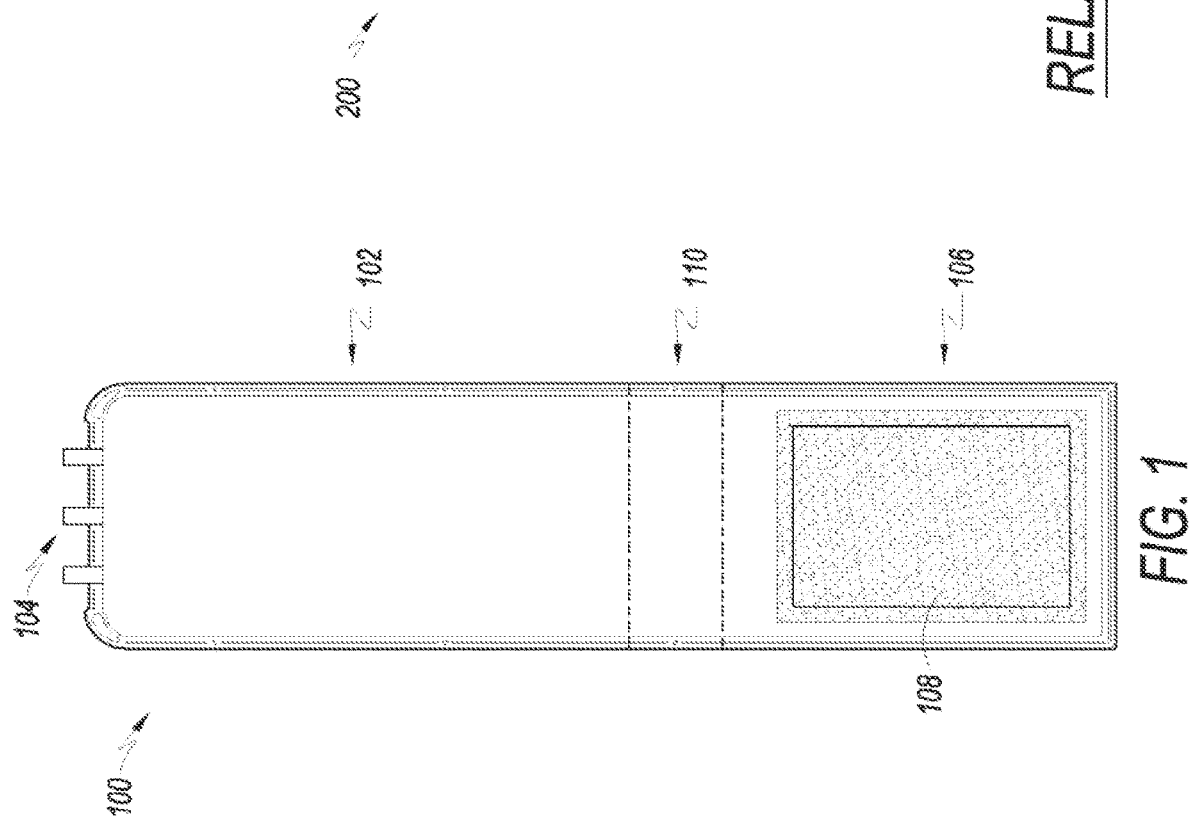

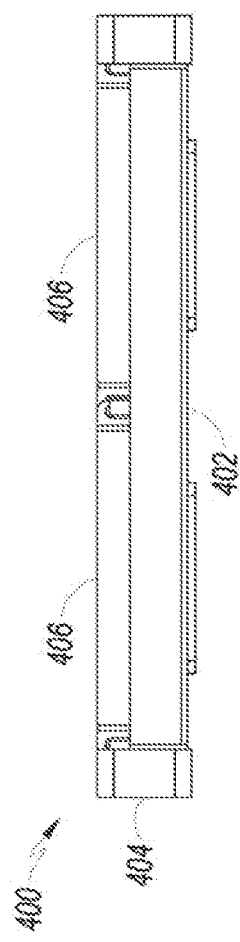
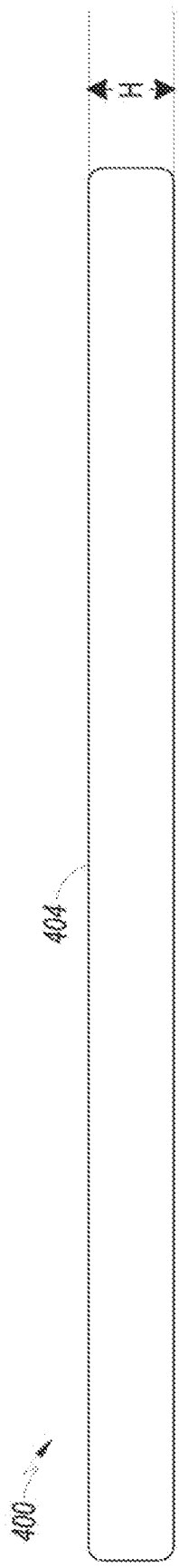
FIG. 4A
FIG. 4B

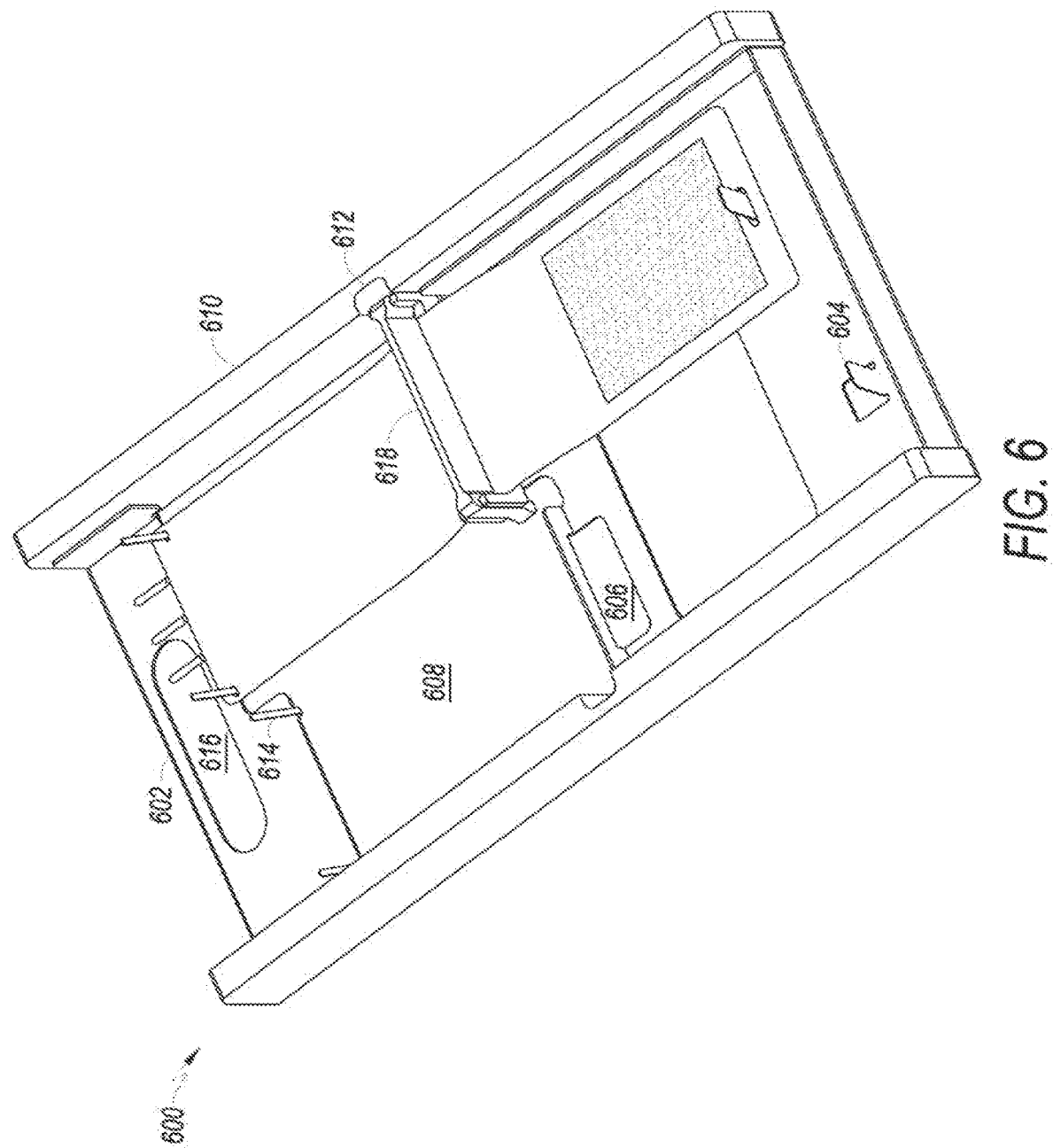

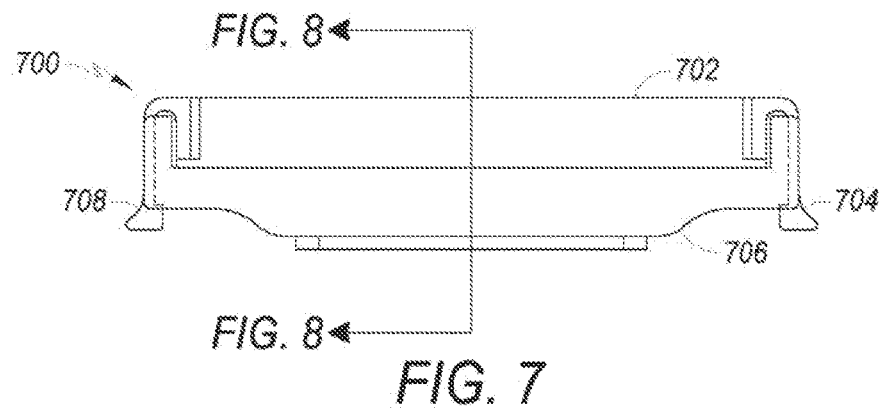
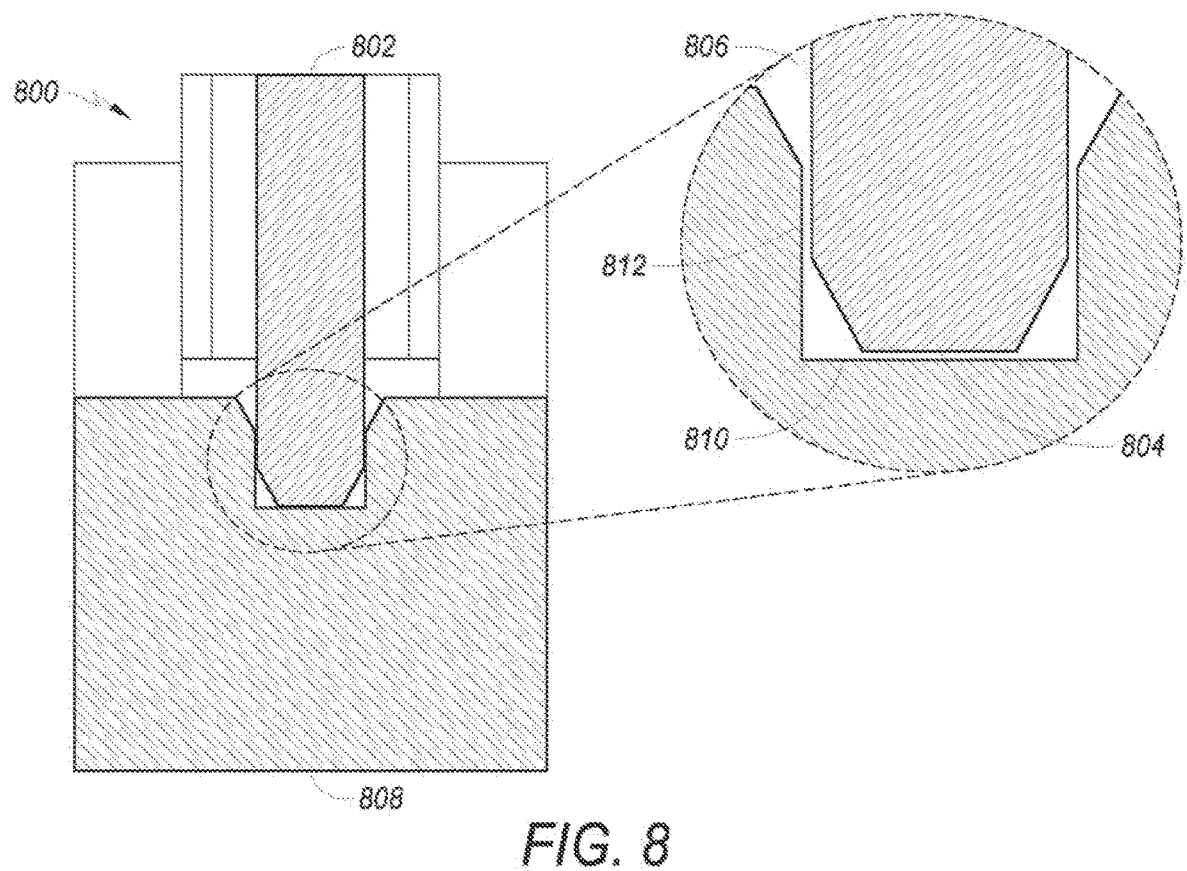

LYOPHILIZATION LOADING TRAY ASSEMBLY AND SYSTEM

CROSS-REFERENCE TO RELATED APPLICATIONS

This application is a continuation of U.S. patent application Ser. No. 16/815,880 filed on Mar. 11, 2020, which claims the benefit of the following: U.S. Provisional Application No. 62/818,214, filed on Mar. 14, 2019; U.S. Provisional Application No. 62/952,752 filed Dec. 23, 2019; and U.S. Provisional Application No. 62/971,072 filed Feb. 6, 2020. The entire disclosures of each of the above applications are incorporated herein by reference.

The invention was made with government support under contract number H92222-I6-C-008 I awarded by the United States Department of Defense. The government has certain rights in the invention.

BACKGROUND

The present application describes a loading tray assembly and related system for loading a lyophilization container into a lyophilizer and lyophilizing a fluid. The loading tray assembly is configured to house a flexible, multi-part lyophilization container. The devices and systems described herein are principally designed for the lyophilization of biological fluids, such as human and animal blood and related blood products, such as blood plasma.

Lyophilized blood plasma has been utilized for many decades. Various benefits associated with lyophilized plasma are well known and include logistical and storage advantages, as well as the ability to obtain large quantities of commercially viable product simply, safely, and rapidly. A flexible, multi-part container including a breathable membrane for use in the lyophilization of plasma is known in the art. In operation, a number of variables may impact the performance of such a container. In one aspect, an optimal contact between the container and a lyophilizer shelf may not be achieved or maintained throughout the lyophilization process, resulting in less-than-optimal container performance and a diminished yield of viable product. In another aspect, operator error may affect container performance. For instance, an operator may fail to create an occlusion in the container for isolating the lyophilizate after sublimation and desorption, resulting in a fouling of the breathable membrane or an ingress of contaminants into the container. For these and other reasons, there remains a need to develop techniques and devices capable of optimizing lyophilization container performance and of reducing the potential for operator error throughout the lyophilization process.

Although specific embodiments of the present application are provided in view of these and other considerations, the specific problems discussed herein should not be interpreted as limiting the applicability of the embodiments of this disclosure in any way.

SUMMARY

This summary is provided to introduce aspects of some embodiments of the present application in a simplified form and is not intended to comprise an exhaustive list of all critical or essential elements of the claimed invention, nor is it intended to limit the scope of the claims.

Embodiments provide for a loading tray assembly for housing a lyophilization container. The loading tray assembly comprises a chassis including a contact void configured to facilitate direct contact between the attached container and a lyophilizer shelf, a temporary clamp and a shelf spacer.

In another aspect, a system is provided including a multi-part lyophilization container, a loading tray assembly and a lyophilizer. The lyophilization loading tray assembly includes a chassis including contact void configured to facilitate direct contact between the attached multi-part lyophilization container and a lyophilizer shelf.

In yet another aspect, a method is provided including the steps of securing, on a lyophilization loading tray assembly, a multi-part lyophilization container including a peelable seal, inputting a liquid into a non-breathable section of the lyophilization container, freezing the liquid, applying heat energy and a vacuum, the vacuum causing an opening of the peelable seal of the lyophilization container and allowing vapor transfer between a non-breathable section of the container and a breathable section of the container and occluding the multi-part lyophilization container to isolate the frozen liquid.

Further embodiments of the present application include additional methods and devices and systems for lyophilizing fluids. The fluid may be any suitable liquid, including human or animal plasma.

DRAWINGS

Non-limiting and non-exhaustive embodiments are described with reference to the following figures.

FIG. 1 is an illustration of a flexible multi-part lyophilization container according to the related art;

FIG. 2 is an illustration of a lyophilizer according to the related art;

FIGS. 4A and 4B are alternative views of a loading tray assembly according to an embodiment of the present application;

FIG. 6 is a perspective view of a loading tray assembly housing a lyophilization container according to an embodiment of the present application;

FIG. 7 is a front view of a temporary clamp according to an embodiment of the present application;

FIG. 8 is a side section view of a temporary clamp according to an embodiment of the present application;

DETAILED DESCRIPTION

Figure 3A:
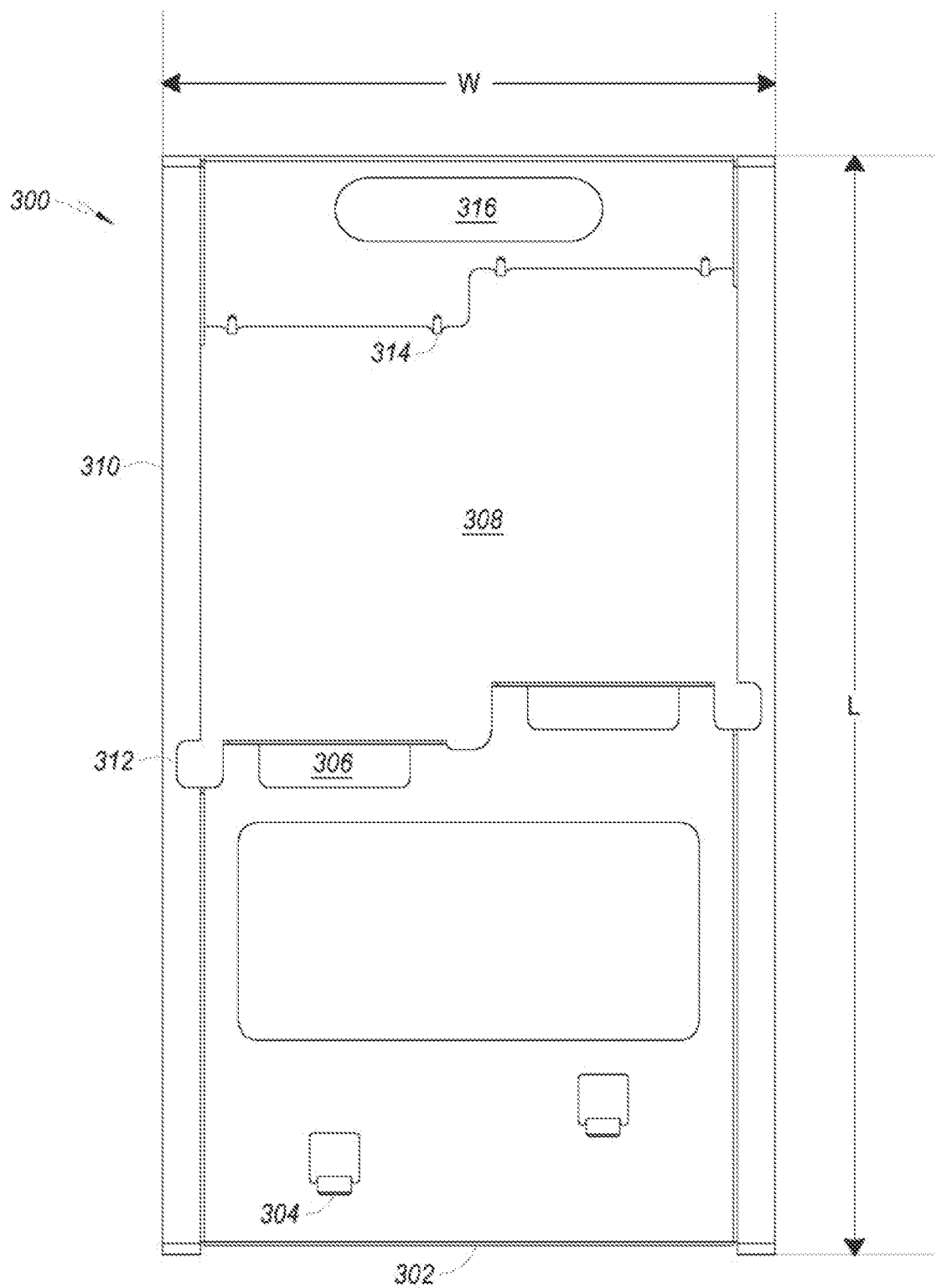
FIGS. 3A and 3B are alternative plan views of a loading tray assembly according to an embodiment of the present application.

The principles described in the present application may be further understood by reference to the following detailed description and the embodiments depicted in the accompanying drawings. Although specific features are shown and described below with respect to particular embodiments, the present application is not limited to the specific features or embodiments provided. Moreover, embodiments below may be described with respect to lyophilizing and storing human or animal blood or blood components; however, such descriptions are merely illustrative. Those of skill in the art will appreciate that embodiments of this disclosure may be used in connection with the lyophilization of any suitable liquid.

Embodiments of the present application refer to a specialized tray assembly for loading a lyophilization container into a lyophilizer and for facilitating an evolution of the container throughout a lyophilization process. The tray assembly includes a temporary clamp designed to create a temporary occlusion in the lyophilization container after sublimation and desorption in order to prohibit contamination of the lyophilizate.

Embodiments described in this application may be implemented in conjunction with many conventional, commercially available lyophilizers, such as the Magnum® Pilot lyophilizer by Millrock Technology. Accordingly, the devices and techniques described in this application may be more accessible and more widely distributed than those presently in existence. Further advantages of the various enumerated embodiments are noted throughout this disclosure.

FIG. 1 is an illustration of a flexible multi-part lyophilization container according to the related art.

Referring to FIG. 1, the lyophilization container 100 includes a non-breathable section 102; including a port region 104; a breathable section 106, including a breathable membrane 108; and an occlusion zone 110.

In operation, lyophilization container 100 exchanges fluids via ports positioned in the port region 104 of non-breathable section 102. Fluid exchanges occur during initial filling of the container with liquid plasma and during the post-lyophilization filling of the container with sterile water for reconstitution and transfusion into a patient. Non-breathable section 102 and breathable section 106 are isolated from one another by a creation of an occlusion of the container in the occlusion zone 110 encompassing the transition between the non-breathable section 102 and breathable section 106. In this respect, the position of the occlusion within the occlusion zone 110 defines the boundary between non-breathable section 102 and breathable section 106.

The lyophilization container 100 is configured to continually evolve throughout the lyophilization process. The devices and techniques of the present application are designed to facilitate the evolution and optimal performance of the lyophilization container 100. Accordingly, the container may further include a variety of conventional positioning and securing means for cooperating with complimentary features of a loading tray assembly. To cooperate with the loading tray assembly variously shown and described throughout this application, the container 100 will have a hanger hole and positioning holes (not shown) designed, respectively, to compliment hanger tabs and positioning tabs described below.

FIG. 2 is an illustration of a generic lyophilizer according to the related art.

Referring to FIG. 2, the lyophilizer 200 comprises timing and temperature controls 202; and a hydraulic shelf system 204.

The lyophilizer shown in FIG. 2 is an example of a conventional lyophilizer suitable for use in conjunction with embodiments of the present application. Typical components of suitable conventional lyophilizers include timing and temperature controls, a refrigeration system, a vacuum system, a condenser and a chamber including a hydraulic shelf system capable of lyophilization and stoppering.

Figure 3B:
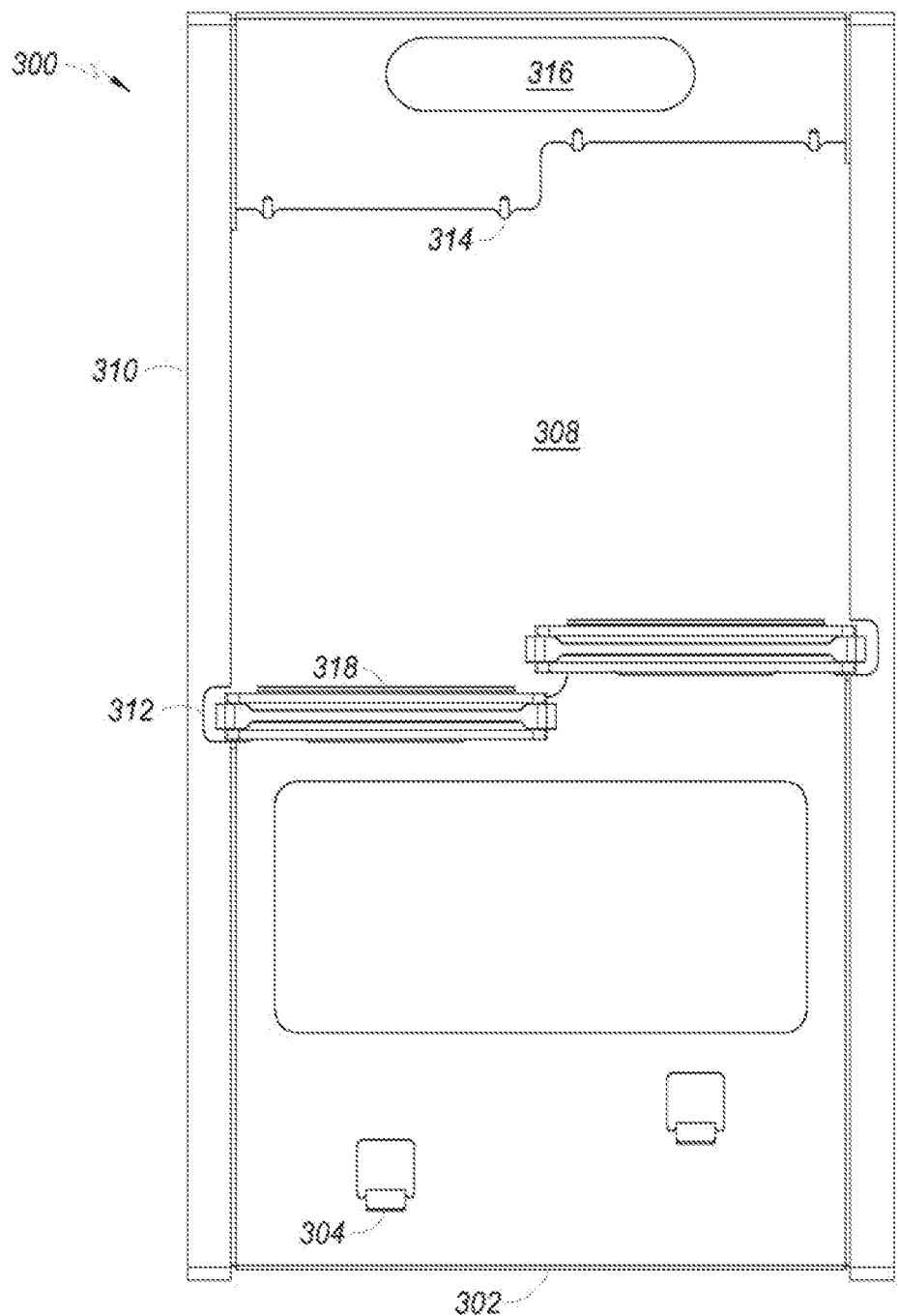

FIG. 3A and FIG. 3B are alternative plan views of a loading tray assembly according to an embodiment of the present application.

Referring to FIG. 3A, the loading tray assembly 300 comprises tray chassis 302; hanger tabs 304; clamp seats 306; contact voids 308; shelf spacers 310, including clamp indentations 312; positioning tabs 314; and a handle 316. FIG. FIG. 3B illustrates an embodiment of the loading tray assembly of FIG. 3A including a temporary clamp. Referring to FIG. 3B, the loading tray assembly 300 comprises tray chassis 302; hanger tabs 304; contact voids 308; shelf spacers 310, including clamp indentations 312; positioning tabs 314; a handle 316; and two-piece temporary clamps 318.

The loading tray assembly 300 shown in FIGS. 3A and 3B is essentially rectangular in shape and is configured to secure two flexible, multi-part lyophilization containers. Tray chassis 302 provides the essential structural support of the loading tray assembly 300. Hanger tabs 304 are rectangular protrusions extending upward from tray assembly 300 and are configured to engage a complimentary hanger hole of a lyophilization container. Clamp seats 306 are cut-out or void regions of tray chassis 302 configured to allow a bottom portion of temporary clamp 318 to seat therein. Contact voids 308 are also cut-out or void regions of tray chassis 302 and are configured to allow direct contact between a secured lyophilization container and a lyophilizer shelf. Shelf spacers 310 are affixed to the lateral sides of the chassis 302 of the loading tray assembly 300 and support both an effective clamp closure and an even, parallel collapse of lyophilizer shelves. Shelf spacers 310 include clamp indentations 312 adjacent to clamp seats 306 to accommodate seated clamps 318. Positioning tabs 314 cooperate with hanger tabs 304. Positioning tabs 314 are rectangular protrusions extending upward and are configured to engage positioning holes of a lyophilization container. Handle 316 is a cut-out or void region configured to accommodate the hand of an operator for handling of the loading tray assembly. Temporary clamp 318 is a two-piece clamp configured to create an occlusion in a lyophilization container during lyophilization.

In FIGS. 3A and 3B, the dimensions (i.e., length and width) of the tray assembly 300 are respectively denoted as "L" and "W". In a preferred embodiment, assembly length is approximately 60 cm and assembly width is approximately 30 cm. However, in alternative embodiments, tray assembly dimensions may vary. For instance, assembly length may be between 45 cm and 75 cm, such as between 55 and 65 cm, whereas tray assembly width may be between 20 cm and 40 cm, such as between 25 and 35 cm.

In embodiments, tray assembly 300 design is not limited; tray assembly 300 and its individual features may be adapted for a particular application. For instance, contact voids 308 may be enlarged for the purpose of reducing the thermal mass of the chassis 302, and accordingly, minimizing the impact of the chassis 302 on heat transfer from the lyophilizer shelf to the product. In further embodiments, handle 316 may be enlarged to accommodate a gloved hand, or may include additional features (e.g., finger grooves) designed for improved handling. In yet further embodiments, tray assembly 300 may vary in shape and may be configured to house any number of lyophilization containers. For instance, tray assembly 300 may be configured to house lyophilization containers having a variety of dimensions and may house such containers in a front-to back configuration as opposed to a side-by-side configuration.

As shown in FIGS. 3A and 3B, feature groupings for each of the respective containers to be attached (i.e., hanger tabs 304, clamp seats 306, contact voids 308, clamp indentation portions 312 and positioning tabs 314) are offset from one another. The inclusion of offset feature groupings allows multiple lyophilization containers to be secured in the tray assembly absent any interference among the respective clamps 318. Accordingly, this configuration also supports maximum lyophilization container width, thereby improving overall system efficiency.

FIGS. 4A and 4B are, respectively, a front view and a side view of a loading tray assembly according to an embodiment of the present application.

Referring to FIG. 4A, tray assembly 400 includes a tray chassis 402; shelf spacers 404 and two-part clamp 406. FIG. 4B is a side view of loading tray assembly 400 showing a shelf spacer 404.

The height of the shelf spacer 404, denoted as "H," is approximately 3.5 cm. As shown, the height of the shelf spacer 404 defines the overall height of the tray assembly 400 when the clamp 406 is in an actuated or closed state. In operation, the height of the shelf spacer 404 also defines the minimum distance between lyophilizer shelves during shelf collapse. Accordingly, to achieve an optimal clamp closure, the height of the shelf spacer 404 must be coincident to the height of the actuated clamp 406. In various embodiments, the height of shelf spacer 404 may be between 2.5 cm and 4.5 cm, such as between 3.0 cm and 4.0 cm.

Shelf spacers 404 serve multiple functions. One function of shelf spacers 404 is to control the distance between lyophilizer shelves in a collapsed state. If shelf spacer 404 height is too large, a full occlusion of an attached lyophilization container may not be achieved. In contrast, if shelf spacer 404 height is too short, the two-part clamp 406 may be crushed by the collapsing lyophilizer shelves. Another function of shelf spacers 404 is to eliminate shelf tilt and binding which can occur during shelf collapse. That is, lyophilizer shelves are essentially horizontal plates disposed parallel to one another in a stacked configuration. Under pressure from a hydraulic ram or other actuation means, the lyophilizer shelves collapse vertically, stacking on top of one another. If not maintained substantially parallel to one another during collapse, the shelves may tilt and jam or bind. To address this problem, shelf spacers 404 provide a hard stop along a considerable length of the shelf to ensure that the shelves are maintained substantially parallel to one another throughout operation. In various embodiments, the position of shelf spacers is not limited. For example, embodiments may incorporate shelf spacers on alternative sides of the tray assembly 400. In yet further embodiments, shelf spacers 404 may be positioned only on tray assembly 400 corners or positioned around the perimeter of tray assembly 400.

As shown in FIG. 4A, the bottom surface of the tray chassis 402 is not coincident to the bottom surface of shelf spacers 404. That is, bottom surface of tray chassis 402 is offset from the bottom surface of shelf spacers 404 in order to maintain a space between tray chassis 402 and a lyophilizer shelf during lyophilization. In embodiments, the bottom surface of tray chassis 402 is offset from a bottom surface of shelf spacers by a distance of between 0.02 mm and 5.0 mm, such as by 1 mm. Maintaining this space eliminates conductive energy transfer between the tray chassis 402 and the lyophilizer shelf, thereby reducing overall thermal transfer to the tray assembly 400 during lyophilization. Reducing thermal transfer to the tray assembly 400 allows for more rapid freezing and heating and allows for more precise control of the lyophilization process.

Figure 5:
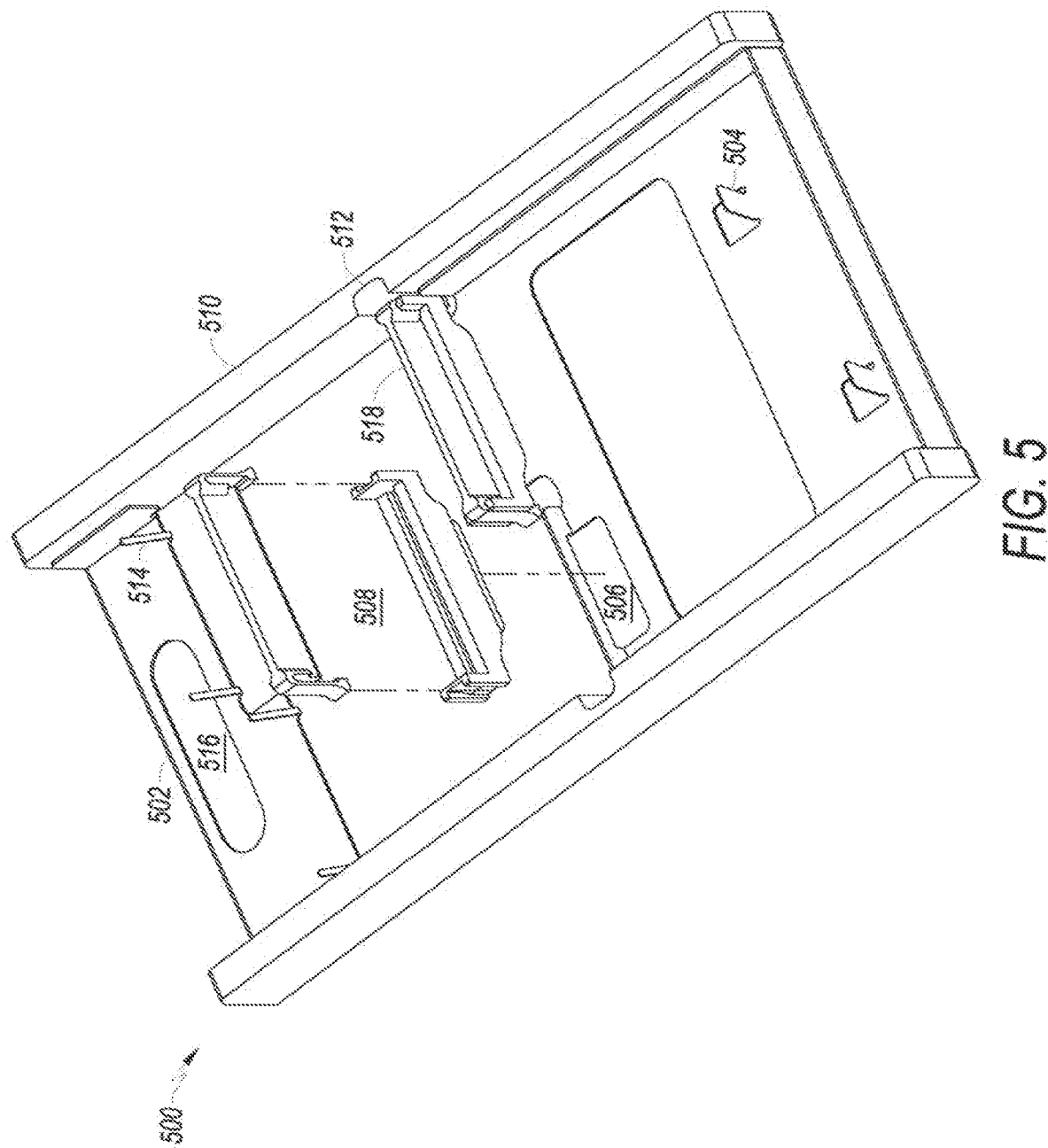
FIG. 5 is a partial exploded view of a loading tray assembly according to an embodiment of the present application.

FIG. 5 is a partially exploded view of a loading tray assembly according to an embodiment of the present application.

Referring to FIG. 5, the loading tray assembly 500 includes tray chassis 502; hanger tabs 504; clamp seats 506; contact voids 508; shelf spacers 510, including clamp indentation portions 512; positioning tabs 514; a handle 516; and a two-piece temporary clamp 518.

During initial set up, clamp 518 is configured to have an open bias. That is, top jaw of clamp 518 is manually rested on the bottom jaw of clamp 518 by an operator, forming a void space therebetween. In operation, actuation of the clamp 518 occurs as collapsing lyophilizer shelves force the top and bottom clamp jaws into engagement with one another. As noted above, the shelf spacers 510 assist in the actuation of the clamp 518 by providing a stopping mechanism at a height which allows for the actuation of the clamp 518, yet which prevents shelf tilt and binding, and which obviates the potential for crushing of the clamp 518 and container during shelf collapse.

The embodiment of the clamp shown in FIG. 5 is configured to be manually set-up, to be mechanically actuated by collapsing lyophilizer shelves, and to be manually released after a permanent seam is created in the lyophilization container. Alternative embodiments are not limited and may utilize another clamp or clamping scheme. For instance, any of clamp set-up, clamp actuation or clamp release may be performed using alternative mechanical or electro-mechanical means. For example, top and bottom clamp jaws may be connected by a conventional hinge or connected by any other suitable means. In further embodiments, a means for clamp set-up or for clamp release may be integrated into a lyophilizer shelf system.

In the configuration shown in FIG. 5, shelf spacers 510 are attached to the tray chassis 502 using conventional screws. However, in alternative embodiments, assembly 500 may be formed as a single component including shelf spacers 510 or may integrate shelf spacers 510 using any other conventional fasteners, such as adhesives or bolts. A preferred material choice for tray chassis 502 is aluminum; however, alternative metals, metal alloys and plastics capable of providing similar structural rigidity may be used. In the embodiment shown, shelf spacers 510 are injection molded and cored using conventional techniques to minimize mass. Shelf spacers comprise a blend of Polycarbonate (PC) and Acrylonitrile Butadiene Styrene (ABS). A principal advantage of the PC/ABS blend is its ability to be loaded, without scratching, on to a lyophilizer shelf that includes a surface treatment or coating. The use of plastic in shelf spacers also improves heat transfer between the lyophilizer shelf and the product during sublimation and desorption by minimizing heat losses to the loading tray assembly. In further embodiments, material choices are not limited and may include any material having desirable characteristics and which is capable of functioning in a lyophilizer.

FIG. 6 is a perspective view of a loading tray assembly housing a lyophilization container according to an embodiment of the present application.

Referring to FIG. 6, the loading tray assembly 600 includes tray chassis 602; hanger tabs 604; clamp seats 606; contact voids 608; shelf spacers 610, including clamp indentation portions 612; positioning tabs 614; a handle 616; and a two-piece temporary clamp 618.

In FIG. 6, a flexible, multi-part lyophilization container as depicted in FIG. 1 is disposed between the top and bottom jaws of clamp 618. As shown, clamp 618 is in a closed or actuated state creating an occlusion between a breathable section and a non-breathable section of the lyophilization container. The lyophilization container is secured to the loading tray assembly 600 using hanger tabs 604 and positioning tabs 614.

The respective engagement of hanger tabs 604 and positioning tabs 614 with a hanger hole and positioning holes of lyophilization container cause the lyophilization container to be accurately and securely positioned within tray chassis 602. Accurate and secure positioning results in optimized container performance. In one aspect, accurate positioning of the lyophilization container within the tray assembly ensures that an occlusion is created in a region of the container designed for the occlusion (e.g., a peel seal region or an occlusion zone). In another aspect, secure positioning of the container via the respective engagement between the hanger tab 602 and positioning tabs 614 of the tray assembly with complimentary hanger hole and positioning holes of the lyophilization container enables optimal longitudinal container tension to be obtained. Optimizing container tension is a factor in optimizing the surface area of the contact patch between the lyophilization container and a lyophilizer shelf via contact void 608. An optimized surface area of the contact patch results in improved heat transfer during freezing, primary drying and secondary drying. In contrast, a lower-than-optimal longitudinal container tension may cause the lyophilization container to sag, resulting in an incorrect longitudinal position and the potential creation of an occlusion in an unsuitable region of the container. A higher-than-optimal longitudinal container tension may result in a contact patch having an inadequate surface area, resulting in poor conductive heat transfer. Accordingly, an accurate and secure container attachment contributes to ensuring that an occlusion occurs in the correct region of the lyophilization container and that a correct amount of contact occurs between the lyophilization container and the lyophilizer shelf.

In further embodiments, tray assembly 600 features may vary without departing from the teachings of this application. For instance, the size and shape of contact voids 606 may vary to some degree to suit a particular container configuration. Likewise, hanger tab 602 or positioning tabs 614 may be differently positioned, may comprise a different shape or may include additional features to assist in the engagement between the lyophilization container and the tray assembly 600.

There are several advantages to utilizing the described loading tray assembly 600 in a lyophilization process. In one aspect, utilizing the tray assembly 600 results in an optimized and consistent loading of lyophilization containers. A consistent and optimal loading of containers is important in achieving consistent results in batch processes. In another aspect, the automation of clamping is advantageous. The automation of clamping reduces operator error which, in turn, promotes optimal bag performance, reduces the potential for membrane fouling and reduces the potential for an ingress of contamination into the container.

FIG. 7 is a front view of a temporary, two-piece clamp according to an embodiment of the present application.

Referring to FIG. 7, the temporary clamp 700 includes a top jaw 702 with clasp members 704; and bottom jaw 706 with clasp members 708.

Temporary clamp may be described as a two-piece guillotine clamp or a parallel clamp. Each of top jaw 702 and bottom jaw 706 respectively includes vertically oriented, slide release buckle clasp members 704, 708 configured to engage one another. When in its initial position, the bottom jaw is seated within the clamp seat of the tray assembly and top jaw 702 is rested on bottom jaw 706. When in its actuated position, top jaw 702 and bottom jaw 706 buckle clasp members 704, 708 are engaged with one another. Top and bottom jaws 702, 706 are accordingly disposed substantially parallel to one another and parallel to the tray assembly in both the open position and the closed position.

Preferably, temporary clamp is injection molded using Acrylonitrile Butadiene Styrene (ABS). However, in alternative embodiments, alternative manufacturing methods and plastics exhibiting similar characteristics may be desirable.

An exemplary clamping workflow is as follows: First, the lyophilization loading tray assembly is partially assembled. In this step, the bottom jaw of two-part clamp is seated in the clamp seat of the lyophilization tray assembly. Next, a lyophilization container including a peelable seal is loaded on to the tray assembly. In this step, the lyophilization container is rested on the bottom clamp jaw and each of positioning tabs and hanger tab of the tray assembly engage complimentary features of the container. Next, the top jaw of the two-part clamp is rested on the bottom jaw, forming an "open" clamp configuration. In this step, the clasp members 704, 708 are not engaged and the lyophilization container extends longitudinally through the void space between the open clamp jaws. Next, the tray assembly and container are loaded into a lyophilizer. Next, the lyophilizer shelves are collapsed, forcing the top jaw of the clamp downward on to the bottom jaw, engaging clasp members 704, 708. In this step, an occlusion is created in the container. Next, the lyophilizer shelves are spaced apart. Next, the occlusion is removed by a manual release of clasp members 704, 708, creating space between top and bottom clamp jaw.

FIG. 8 is a side section view of a temporary clamp according to an embodiment of the present application.

Referring to FIG. 8, clamp 800 comprises a top jaw 802, including horizontal member 804 and lateral members 806; and a bottom jaw 808, including horizontal member 810 and lateral members 812.

As shown in FIG. 8, top and bottom jaw members are configured to cooperate with each other in the creation of an occlusion. In this configuration, two occlusions are made when the clamp is actuated. That is, upon clamp actuation, the flexible container material between top jaw 802 and bottom jaw 808 is occluded at both interfaces between lateral members 806, 812. Advantageously, two points of occlusion create a redundancy, thereby increasing both clamp reliability and quality.

In the actuated or closed state, the tolerance between lateral members 806, 812 of the top jaw 802 and of the bottom jaw 808 must reliably occlude a lyophilization container yet must not compromise container materials (i.e., tear or rip). In a preferred embodiment, the tolerance between lateral members of the top and bottom jaws may be between 80 percent and 99 percent of the thickness of the two layers of container material. In the actuated or closed state, the tolerance between horizontal member 804 of the top jaw 802 and the horizontal member 810 of the bottom jaw 808 does not occlude the lyophilization container and should provide a space for container material. In a preferred embodiment, the tolerance between horizontal members 804, 810 of the top and bottom jaws 802, 808 is greater than 100 percent of the thickness of the two layers of clamped container material, such as between 101 percent and 120 percent of the thickness of the two layers of clamped container material.

Figure 9:
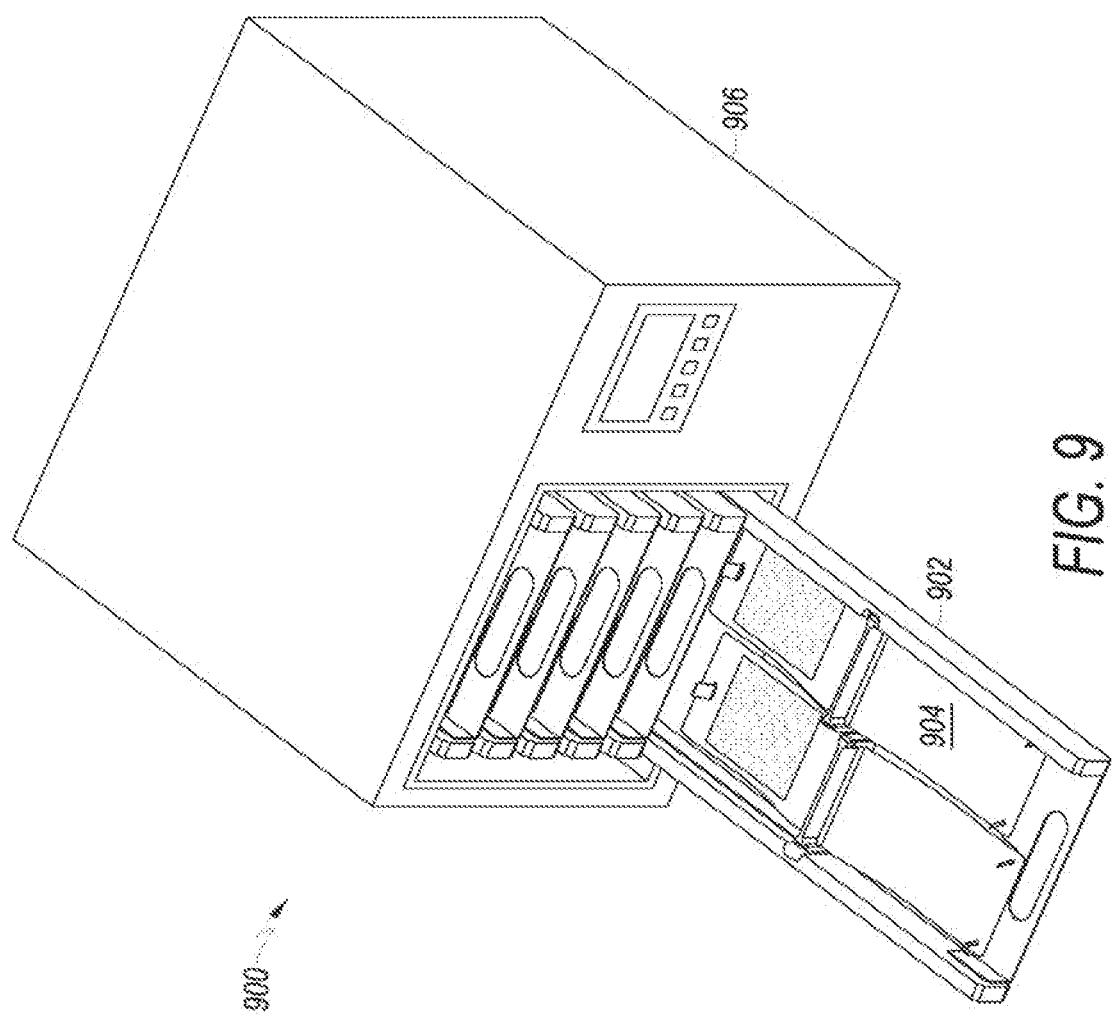
FIG. 9 is an illustration of a lyophilization system according to an embodiment of the present application.

FIG. 9 is an illustration of a lyophilization system according to an embodiment of the present application.

Referring to FIG. 9, the lyophilization system 900 includes a loading tray assembly 902; a flexible multi-part lyophilization container 904; and a lyophilizer 906.

As shown in FIG. 9, the loading tray assembly 902 of the present application is used to house a multi-part lyophilization container 904 of the related art. Once the lyophilization container is housed in the tray assembly 902, the tray assembly 902 is loaded into a suitable conventional lyophilizer 906.

Exemplary workflows included below describe the manner in which the loading tray assembly 902, in conjunction with shelves of the lyophilizer 906, automates a clamping function and optimizes the performance of the lyophilization container as the container evolves throughout the lyophilization cycle.

Figure 10:
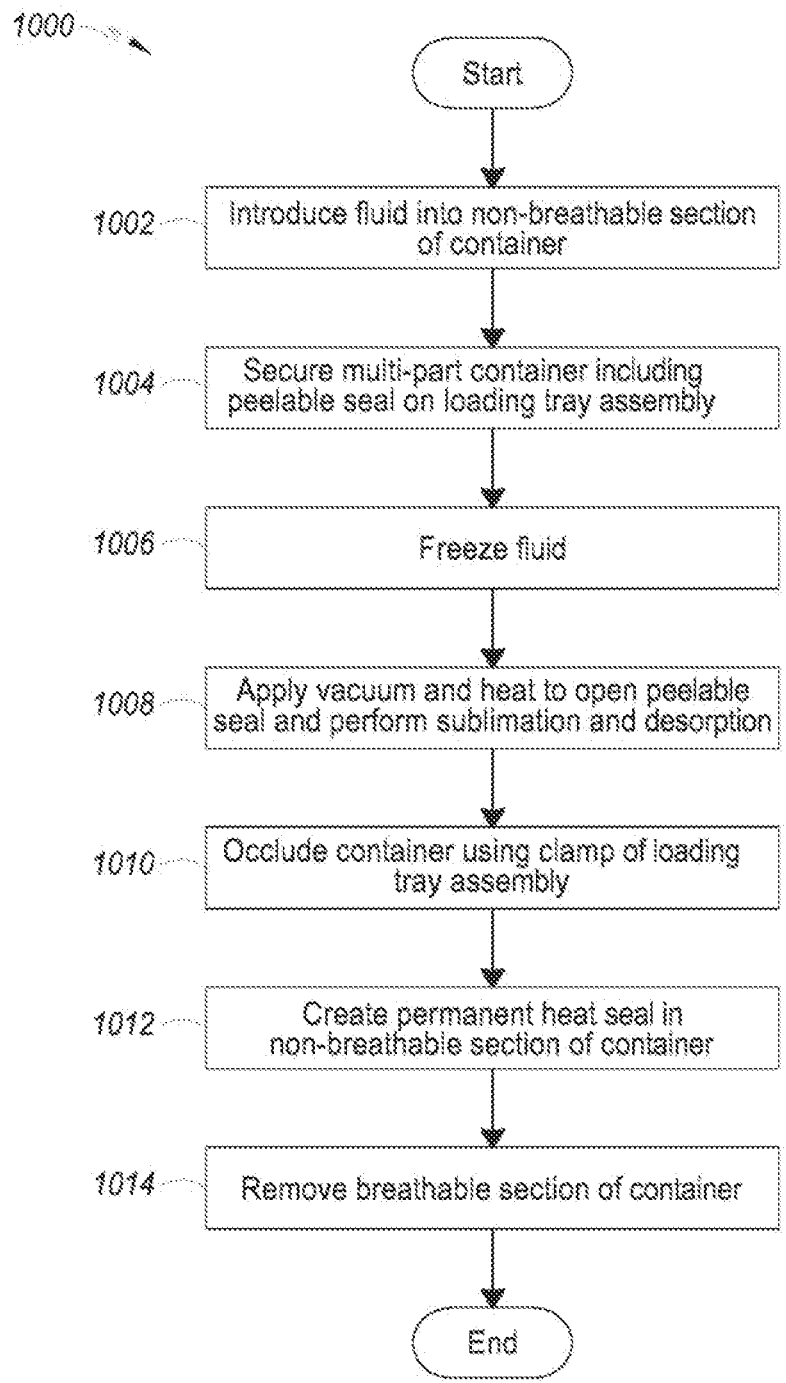
FIG. 10 is a workflow schematic according to an embodiment of the present application.

FIG. 10 is a workflow schematic according to an embodiment of the present application.

Referring to workflow 1000 shown in FIG. 10, a subject fluid (e.g., blood plasma) is introduced into a non-breathable section of the lyophilization container in step 1002. In step 1004, a multi-part lyophilization container including a peelable seal and an occlusion zone is secured on a lyophilization loading tray assembly. In step 1006, the fluid in the container is frozen, creating a thin, uniform structure of ice in the non-breathable section. In step 1008, vacuum and heat energy are applied. The vacuum removes or "opens" the peelable seal, and along with the heat energy, is used to perform sublimation and desorption, causing a phase change in the ice structure from the solid phase directly to the vapor phase. Vapor released from the ice structure flows through the container cavity and escapes through the breathable section, leaving the lyophilized plasma cake (i.e., the ice structure now dehydrated as a result of lyophilization) in the non-breathable section. In step 1010, the container is occluded by the actuation of a two-part clamp of the loading tray assembly. In step 1012, a permanent seam is created in non-breathable material of the breathable section. In step 1014, the container is divided at the permanent seam and the breathable section is discarded, leaving the lyophilizate in the non-breathable section.

In step 1002, the introduction of fluid may be referred to as preloading. During preloading, between 250 ml to 500 ml of fluid (e.g., blood plasma) are input into the non-breathable section of the multi-part lyophilization container.

In step 1004, the securing of the lyophilization container on the loading tray assembly includes disposing the lyophilization container on the tray assembly, through an open space between a top jaw and a bottom jaw of a two-piece clamp seated in the loading tray assembly and engaging complimentary positioning features built into the tray assembly and the container. Notably, step 1002 and step 1004 may be reversed in certain embodiments.

In step 1008, vacuum pressure and heat energy are applied. Since the vacuum pressure required for lyophilization is lower than the vacuum pressure required to open the peelable seal, no special vacuum adjustments are necessary. That is, as vacuum is applied to the lyophilizer chamber, the peelable seal is opened before lyophilization pressures are achieved. In this regard, the application of vacuum and heat energy together cause sublimation and desorption to proceed in the usual manner. Preferable drying temperatures may range from −20° C. to −40° C., such as −25° C.

In step 1010, the container is occluded by the actuation of a two-part clamp. The two-part clamp is actuated by a collapse of the lyophilizer shelves. That is, shelf collapse forces the top clamp jaw downward into engagement with the bottom clamp jaw. Actuation in this manner is possible insofar as the initial state of the clamp is an open state. The purpose of creating an occlusion in this step is primarily to prevent contamination of the lyophilizate with moisture and oxygen from air prior to step 1012.

In step 1012, a permanent seam is created, isolating the lyophilized cake in the non-breathable section. In the schematic shown, permanent seam step 1014 is a discreet step. That is, an ancillary piece of equipment is used to create the permanent seam or seal. In further examples, permanent seam step 1014 may be integrated into occlusion step 1012. In such embodiments, the occlusion means (e.g., a clamp) may incorporate the permanent sealing means.

In step 1014, the complete removal of the breathable section represents the final evolution of the container. Notably, steps 1012 and 1014 may optimally not occur in various embodiments.

In further exemplary workflows, steps may be added to the workflow described in FIG. 10. For example, additional steps may include the introduction of gas into the lyophilization container to regulate pH or to create a vapor space above the subject fluid or ice structure. An additional step may also include the backfilling of the lyophilization container with an inert gas to regulate container pressure.

Figure 11:
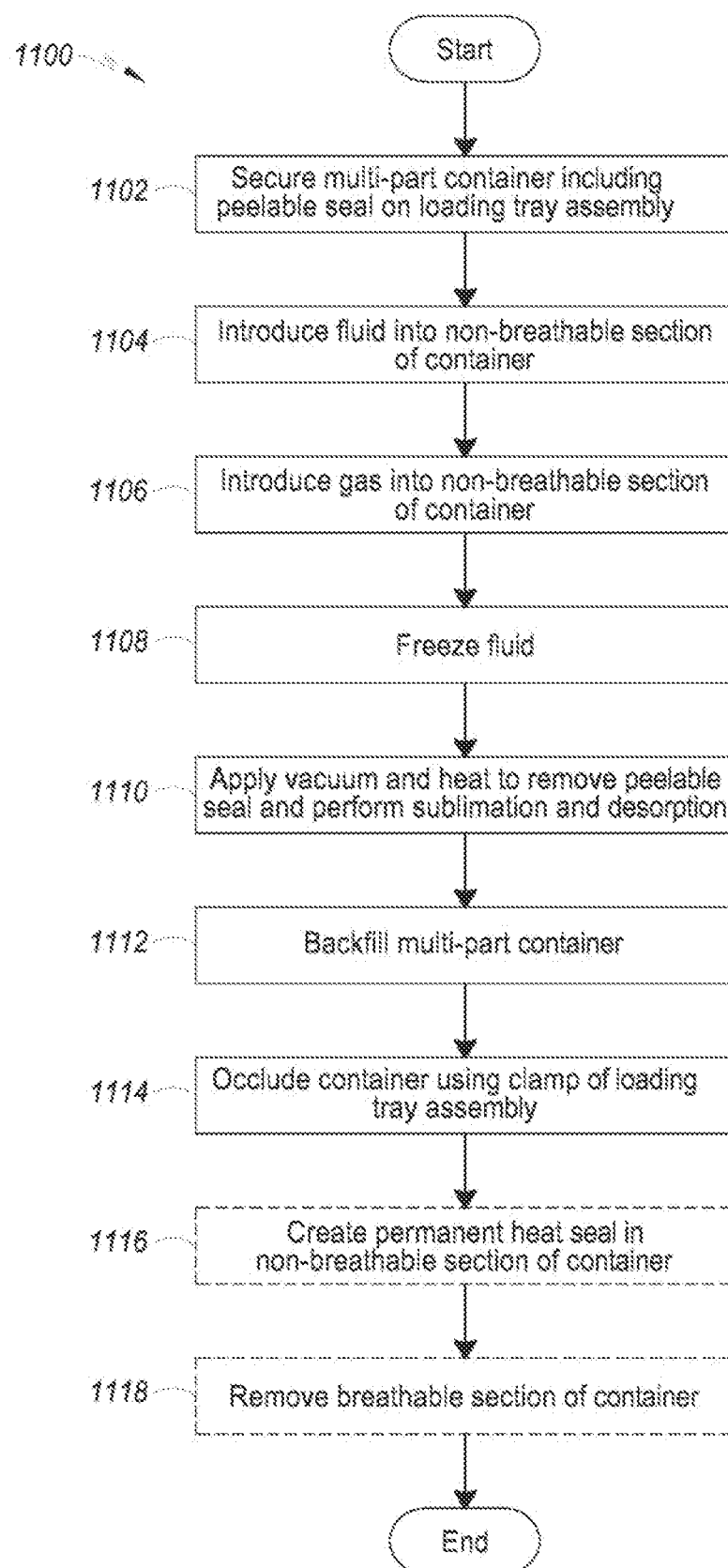
FIG. 11 is workflow schematic according to another embodiment of the present application.

FIG. 11 is workflow schematic according to another embodiment of the present application.

Referring to workflow 1100 shown in FIG. 11, in step 1102, a multi-part lyophilization container including a peelable seal and an occlusion zone is secured on a lyophilization loading tray assembly. In step 1104, a subject fluid (e.g., blood plasma) is introduced into a non-breathable section. Notably, step 1102 and step 1104 may be reversed in certain embodiments. In step 1106, air, inert gas, or a pH regulating gas (e.g., $CO_2$) is introduced into the non-breathable section of the lyophilization container. In step 1108, the fluid in the container is frozen, creating a thin, uniform structure of ice in the non-breathable section. In step 1110, vacuum and heat energy are applied. The vacuum removes or "opens" the peelable seal, and along with the heat energy, is used to perform sublimation and desorption, causing a phase change in the ice structure from the solid phase directly to the vapor phase. Vapor released from the ice structure flows through the container cavity and escapes through the breathable section, leaving the lyophilized plasma cake (i.e., the ice structure now dehydrated as a result of lyophilization) in the non-breathable section. In step 1112, the container is backfilled with an inert gas to raise container pressure to partial or full atmospheric pressure. In step 1114, the container is occluded by the actuation of a two-part clamp of the loading tray assembly. Optionally, in step 1116, a permanent seam is created in the non-breathable material of the breathable section. Optionally, in step 1118, the container is divided at the permanent seam and the breathable section is discarded, leaving the lyophilized end-product in the non-breathable section.

FIG. 11 essentially represents a departure from the workflow of FIG. 10 only in the addition of steps 1106 and 1112. In step 1106, air (or nitrogen or another inert dry gas), or a pH regulating gas (e.g., $CO_2$) is introduced into the lyophilization container. A pH-regulating gas may be introduced to the lyophilization container to regulate pH. In an alternate embodiment, a pH-regulating gas might be introduced during step 1112.

In step 1112, the lyophilization container is backfilled to partial or full atmospheric pressure with pH regulating gas (e.g., $CO_2$). In the case of backfilling to a partial atmospheric pressure, the container is occluded once the desired partial atmospheric pressure is reached. Optionally, the container is then permanently sealed. Occlusion and/or sealing of the container while at a pressure lower than atmospheric pressure causes the container to collapse and reduce its volume when the container is exposed to atmospheric pressure. This process also secures the pH regulating gas in the non-breathable portion and prevents an ingress of oxygen and moisture into the container. Since the resultant container has been occluded and/or sealed at a pressure that is less than atmospheric pressure, and since final container volume will be in a reduced volume condition once the vacuum of the lyophilizer is removed, the final lyophilized product can be stored and transported more easily. Backfilling in this manner is particularly applicable to container embodiments having flexible materials or components since such a diminution of container volume would not be possible with a rigid, inflexible lyophilization container.

Equipment used in the above-described workflows may vary. For instance, some embodiments may employ an all-in-one lyophilizer, whereas other embodiments may utilize a separate, stand-alone freezer for the freezing step. Likewise, some variation may exist in the order of process steps. For instance, the securing of the flexible container on the loading tray assembly may occur before or after the introduction of fluid into the container.

The use of a physical barrier (e.g., a two-piece guillotine clamp) to segregate fluid in the non-breathable section from the breathable section according to workflows described above eliminates the potential for fluid contact with, and fouling of, the pores of breathable material in the breathable section of the lyophilization container. Fouling can disrupt the sublimation and desorption aspects of lyophilization, thereby increasing total lyophilization time and reducing the ability to obtain a viable lyophilizate. Accordingly, eliminating the potential for fouling leads to a relative increase in vapor flow which, in turn, results in faster freeze drying, a colder ice temperature during primary drying due to an increased sublimative cooling effect and increased retention of proteins and clotting factors.

Various advantages and benefits flow from the automation of clamping as described herein. For instance, the use of collapsing shelves to occlude the lyophilization container obviates certain operator errors including an inadvertent mistiming or omission of the clamping step altogether. Another automation advantage derives from the design of the loading tray assembly itself. For example, shelf spacers facilitate a reliable and error-free collapse of the lyophilizer shelves. This, in turn, results in a consistent clamping of each lyophilization container in the system and further reduces the potential for failures or contamination which may be more often associated with manual clamping.

Notwithstanding the various specific embodiments enumerated in this disclosure, those skilled in the art will appreciate that a variety of modifications and optimizations could be implemented for particular applications. For instance, further embodiments of the present application may include a tray assembly having fewer components than, for example, as are included in the embodiment depicted in FIG. 5. Likewise, the described loading tray assembly may be adapted for loading a variety of lyophilization containers that are not limited by the description of the lyophilization container depicted in the present figures. For example, such a container may be rigid, may comprise one or several parts or compartments and may utilize a variety of materials. Accordingly, embodiments of the loading tray assembly described in this application may optionally exclude any of the shelf spacers, the two-part clamp or the container attachment means. That is, certain embodiments may not require shelf spacers to regulate shelf collapse or clamp actuation. Likewise, certain embodiments may exclude a clamp altogether or utilize another type of clamp, such as a wirelessly controlled electro-mechanical clamp. Yet further embodiments may exclude container attachment means and thus comprise only a chassis having a contact void, or only a chassis having a contact void and optionally a clamp and shelf spacers. Additionally, the present application is not limited to the lyophilization of blood or blood products. That is, the principles of the present application may be applicable to the lyophilization of many fluids. Accordingly, various modifications and changes may be made in the arrangement, operation, and details of the methods and systems of the present application which will be apparent to those skilled in the art.

What is claimed is:

1. A tray assembly for holding a lyophilization container in a lyophilizer, the tray assembly comprising:
   a chassis configured to support the lyophilization container;
   a contact void defined by the chassis, the contact void configured to expose the lyophilization container to the lyophilizer;
   a clamp seat defined by the chassis; and
   a clamp configured to be supported on the chassis by the clamp seat, the clamp movable between an open configuration for receiving the lyophilization container on the clamp and a closed configuration for forming an occlusion in the lyophilization container.

2. The tray assembly of claim 1, the tray assembly further comprising a shelf spacer, the shelf spacer defining an indentation proximate to the clamp seat, the indentation and the clamp seat are both configured to receive the clamp and support the clamp on the chassis.

3. The tray assembly of claim 1, wherein the clamp includes a bottom jaw and a top jaw, the bottom jaw is configured to be seated on the clamp seat and the top jaw is configured to be seated on the bottom jaw.

4. The tray assembly of claim 3, wherein with the lyophilization container on the bottom jaw, the top jaw is configured to be coupled to the bottom jaw to pinch the lyophilization container between the bottom jaw and the top jaw to form the occlusion in the lyophilization container.

5. The tray assembly of claim 3, wherein:
   the bottom jaw includes a bottom horizontal member between two bottom vertical members;
   the top jaw includes a top horizontal member between two top vertical members; and
   in a closed configuration the two top vertical members cooperate with the two bottom vertical members, and the top horizontal member cooperates with the bottom horizontal member, to pinch the lyophilization container between the bottom jaw and the top jaw to form the occlusion in the lyophilization container.

6. The tray assembly of claim 5, wherein the bottom horizontal member defines a receptacle configured to receive the top horizontal member therein in the closed configuration.

7. The tray assembly of claim 6, wherein in the closed configuration, a tolerance between the top horizontal member and the bottom horizontal member is between 80% and 99% of a thickness of the lyophilization container.

8. The tray assembly of claim 6, wherein in the closed configuration, a tolerance between the top horizontal member and the bottom horizontal member is more than 100% of a thickness of the lyophilization container.

9. The tray assembly of claim 1, wherein the clamp seat is a first clamp seat, and the clamp is a first clamp;
   wherein the tray assembly further includes a second clamp seat defined by the chassis; and
   a second clamp configured to be supported on the chassis by the second clamp seat, the second clamp movable between an open configuration for receiving the lyophilization container on the second clamp and a closed configuration for forming an occlusion in the lyophilization container.

10. The tray assembly of claim 9, wherein the second clamp is vertically offset from the first clamp.

11. The tray assembly of claim 1, wherein the contact void is a first contact void, the chassis further defining a second contact void; and
   wherein the clamp seat is between the first contact void and the second contact void.

12. The tray assembly of claim 1, further comprising first retention members at a first end of the chassis and second retention members at a second end of the chassis, the first retention members and the second retention members configured to hold the lyophilization container on the chassis;
   wherein the clamp seat is between the first retention members and the second retention members.

13. The tray assembly of claim 12, wherein the contact void is between the clamp seat and the first retention members.

14. A tray assembly for holding a lyophilization container in a lyophilizer, the tray assembly comprising:
   a chassis configured to support the lyophilization container;
   a contact void defined by the chassis, the contact void configured to expose the lyophilization container to the lyophilizer;
   a clamp seat defined by the chassis; and
   a clamp arranged on the clamp seat, the clamp including a top jaw and a bottom jaw, the bottom jaw configured to receive the top jaw;
   wherein the bottom jaw is configured to support the lyophilization container thereon, and in a closed configuration the top jaw cooperates with the bottom jaw to pinch the lyophilization container between the bottom jaw and the top jaw to form an occlusion in the lyophilization container.

15. The tray assembly of claim 14, the tray assembly further comprising a shelf spacer, the shelf spacer defining an indentation proximate to the clamp seat, the indentation and the clamp seat are both configured to receive the clamp and support the clamp on the chassis.

16. The tray assembly of claim 14, wherein the bottom jaw defines a receptacle configured to receive the top jaw;
   wherein in the closed configuration the top jaw is seated in the receptacle of the bottom jaw.

17. The tray assembly of claim 14, wherein the contact void is a first contact void, the chassis further defining a second contact void; and
   wherein the clamp seat is between the first contact void and the second contact void.

18. A tray assembly for holding a lyophilization container in a lyophilizer, the tray assembly comprising:
   a chassis configured to support the lyophilization container;
   a contact void defined by the chassis, the contact void configured to expose the lyophilization container to the lyophilizer;
   a shelf spacer extending along a side of the chassis, the shelf spacer configured to position the tray assembly on a shelf of the lyophilizer
   a clamp seat defined by the chassis;
   a clamp indentation defined by the shelf spacer opposite to the clamp seat; and
   a clamp arranged on the clamp seat and in the clamp indentation, the clamp including a top jaw and a bottom jaw, the bottom jaw configured to receive the top jaw in a receptacle defined by the bottom jaw;
   wherein the bottom jaw is configured to support the lyophilization container thereon, and in a closed configuration the top jaw cooperates with the bottom jaw to pinch the lyophilization container between the bottom jaw and the top jaw to form an occlusion in the lyophilization container.

19. The tray assembly of claim 18, the bottom jaw includes a bottom horizontal member between two bottom vertical members;
   the top jaw includes a top horizontal member between two top vertical members; and
   in a closed configuration the two top vertical members cooperate with the two bottom vertical members, and the top horizontal member cooperates with the bottom horizontal member, to pinch the lyophilization container between the bottom jaw and the top jaw to form the occlusion in the lyophilization container.

20. The tray assembly of claim 18, further comprising front retention members at a front of the tray assembly and rear retention members at a rear of the tray assembly, the front retention members and the rear retention members on opposite sides of the clamp and configured to hold the lyophilization container to the chassis.

* * * * *